(12) United States Patent
Batchelor

(10) Patent No.: US 9,901,389 B2
(45) Date of Patent: Feb. 27, 2018

(54) OFFSET FORCEPS

(71) Applicant: GYRUS ACMI, INC., Southborough, MA (US)

(72) Inventor: Kester J. Batchelor, Mound, MN (US)

(73) Assignee: Gyrus ACMI, Inc., Southborough, MA (US)

( * ) Notice: Subject to any disclaimer, the term of this patent is extended or adjusted under 35 U.S.C. 154(b) by 382 days.

(21) Appl. No.: 14/178,569

(22) Filed: Feb. 12, 2014

(65) Prior Publication Data
US 2014/0276804 A1    Sep. 18, 2014

Related U.S. Application Data

(60) Provisional application No. 61/903,500, filed on Nov. 13, 2013, provisional application No. 61/787,731, filed on Mar. 15, 2013.

(51) Int. Cl.
*A61B 18/14* (2006.01)
*A61B 18/08* (2006.01)
(Continued)

(52) U.S. Cl.
CPC ........ *A61B 18/1442* (2013.01); *A61B 18/085* (2013.01); *A61B 2018/00589* (2013.01);
(Continued)

(58) Field of Classification Search
CPC .......... A61B 18/1442; A61B 2018/167; A61B 2018/00589; A61B 2018/1462;
(Continued)

(56) References Cited

U.S. PATENT DOCUMENTS 1,198,958 A    9/1916    Risely
2,042,985 A    6/1936    Gardella
(Continued)

FOREIGN PATENT DOCUMENTS

CN    1149519 A    5/1997
CN    102164556    8/2011
(Continued)

OTHER PUBLICATIONS

Potentially related U.S. Appl. No. 14/589,482, filed Jan. 5, 2015.
(Continued)

*Primary Examiner* — Jaymi Della
*Assistant Examiner* — Eunhwa Kim
(74) *Attorney, Agent, or Firm* — The Dobrusin Law Firm, P.C.

(57) ABSTRACT

An electrosurgical device comprising: forceps including: (i) a first working arm having a contact surface and (ii) a second working arm having a contact surface; wherein the forceps has a first electrical configuration where the contact surface of the first working arm and the contact surface of the second working arm are substantially opposite each other so that the contact surfaces of the forceps can be used to grip an item between the working arms and so that the forceps is configured to deliver a first therapy current through the first working arm, the second working arm, or both; and wherein the forceps has second electrical configuration where the contact surface of the first working arm and the contact surface of the second working arm are askew relative to each other and an electrode edge is formed on at least one side of the forceps so that a second therapy current extends from the electrode edge.

20 Claims, 12 Drawing Sheets

(51) Int. Cl.
*A61B 18/00* (2006.01)
*A61B 18/16* (2006.01)

(52) U.S. Cl.
CPC ............... *A61B 2018/00595* (2013.01); *A61B 2018/146* (2013.01); *A61B 2018/1462* (2013.01); *A61B 2018/167* (2013.01)

(58) Field of Classification Search
CPC ........ A61B 2018/00595; A61B 18/085; A61B 2018/146
See application file for complete search history.

(56) References Cited

U.S. PATENT DOCUMENTS

| | | |
|---|---|---|
| 2,214,984 A | 9/1940 | Bachmann |
| 2,381,084 A | 8/1945 | Slad |
| 2,575,652 A | 11/1951 | Bovee |
| 2,894,424 A | 7/1959 | Vaughan |
| 3,399,583 A | 9/1968 | Hall |
| 3,417,752 A | 12/1968 | Butler |
| 3,465,621 A | 9/1969 | Ladd |
| 3,576,072 A | 4/1971 | Foster |
| 3,643,663 A | 2/1972 | Sutter |
| 3,685,518 A | 8/1972 | Beuerle et al. |
| 3,699,632 A | 10/1972 | Anhalt |
| 3,818,784 A | 6/1974 | McClure |
| 3,913,586 A | 10/1975 | Baumgarten |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Hren et al. |
| 4,318,313 A | 3/1982 | Tartaglia |
| 4,375,218 A | 3/1983 | DiGeronimo |
| 4,407,069 A | 10/1983 | Conners |
| 4,418,692 A | 12/1983 | Guay |
| 4,443,935 A | 4/1984 | Zamba et al. |
| 4,463,759 A | 8/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,655,215 A | 4/1987 | Pike |
| 4,669,470 A | 6/1987 | Brandfield |
| 4,686,980 A | 8/1987 | Williams et al. |
| 4,713,885 A | 12/1987 | Keklak et al. |
| 4,757,612 A | 7/1988 | Peyrot |
| 4,784,136 A | 11/1988 | Klein |
| 4,860,745 A | 8/1989 | Farin et al. |
| 4,896,661 A | 1/1990 | Bogert et al. |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,293,878 A | 3/1994 | Bales et al. |
| 5,318,589 A | 6/1994 | Lichtman |
| 5,342,359 A | 8/1994 | Rydell |
| 5,370,659 A | 12/1994 | Sakashita |
| 5,403,312 A | 4/1995 | Yates et al. |
| 5,413,575 A | 5/1995 | Haenggi |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,443,463 A | 8/1995 | Stern et al. |
| 5,456,695 A | 10/1995 | Herve Dallemagne |
| 5,458,598 A | 10/1995 | Fienberg et al. |
| 5,472,442 A | 12/1995 | Klicek |
| 5,483,952 A | 1/1996 | Aranyi |
| 5,484,435 A | 1/1996 | Fleenor et al. |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,157 A | 5/1997 | Harris |
| 5,658,281 A | 8/1997 | Heard |
| 5,693,052 A | 12/1997 | Weaver |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| 5,810,805 A * | 9/1998 | Sutcu .................. A61B 18/1442 606/45 |
| 5,827,281 A | 10/1998 | Levin |
| 5,884,954 A | 3/1999 | Trozera |
| 5,891,140 A | 4/1999 | Ginn et al. |
| 5,902,301 A | 5/1999 | Olig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,190,386 B1 | 2/2001 | Rydell |
| 6,270,497 B1 | 8/2001 | Sekino et al. |
| 6,273,887 B1 | 8/2001 | Yamauchi et al. |
| 6,325,795 B1 | 12/2001 | Lidemann et al. |
| 6,355,032 B1 | 3/2002 | Hovda et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,458,128 B1 | 10/2002 | Schulze |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |
| 6,652,514 B2 | 11/2003 | Ellman et al. |
| 6,679,882 B1 | 1/2004 | Kornerup |
| 6,689,130 B2 | 2/2004 | Arai et al. |
| 6,695,840 B2 | 2/2004 | Schulze |
| 6,726,686 B2 | 4/2004 | Buysse et al. |
| 6,749,610 B2 | 6/2004 | Kirwan, Jr. et al. |
| 6,752,767 B2 | 6/2004 | Turovskiy et al. |
| 6,773,434 B2 | 8/2004 | Ciarrocca |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,150,749 B2 | 12/2006 | Dycus et al. |
| 7,156,846 B2 | 1/2007 | Dycus et al. |

(56) References Cited

U.S. PATENT DOCUMENTS

| | | |
|---|---|---|
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank |
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 7,998,140 B2 | 8/2011 | McClurken et al. |
| 8,062,292 B1 | 11/2011 | Slater |
| 8,100,894 B2 | 1/2012 | Mucko et al. |
| 8,162,940 B2 | 4/2012 | Johnson |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,267,935 B2 | 9/2012 | Couture et al. |
| 8,328,170 B2 | 12/2012 | Wasinger |
| 8,361,065 B2 | 1/2013 | West et al. |
| 8,361,072 B2 | 1/2013 | Dumbauld et al. |
| 8,485,413 B2 | 7/2013 | Scheib et al. |
| 8,491,626 B2 | 7/2013 | Roy et al. |
| 8,496,603 B2 | 7/2013 | Mamourian |
| 8,568,411 B2 | 10/2013 | Falkenstein et al. |
| 8,628,529 B2 | 1/2014 | Aldridge et al. |
| 8,632,553 B2 | 1/2014 | Sakamoto et al. |
| 8,702,691 B2 | 4/2014 | Weber et al. |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 9,320,563 B2 | 4/2016 | Brustad et al. |
| 9,326,810 B2 | 5/2016 | Shilev et al. |
| 9,358,065 B2 | 6/2016 | Ladtkow et al. |
| 9,439,665 B2 | 9/2016 | Marczyk et al. |
| 9,452,011 B2 | 9/2016 | Batchelor et al. |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2003/0018329 A1 | 1/2003 | Hooven |
| 2003/0144652 A1 | 1/2003 | Baker et al. |
| 2003/0050633 A1 | 3/2003 | Ellman |
| 2003/0097126 A1 | 5/2003 | Woloszko |
| 2003/0109876 A1 | 6/2003 | Yamauchi |
| 2003/0114850 A1 | 6/2003 | McClurken |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2005/0065510 A1 | 3/2005 | Carmel et al. |
| 2005/0113824 A1 | 5/2005 | Sartor |
| 2005/0113825 A1 | 5/2005 | Cosmescu |
| 2005/0113827 A1 | 5/2005 | Dumbauld et al. |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0084973 A1 | 4/2006 | Hushka |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dambauld et al. |
| 2007/0093857 A1 | 4/2007 | Rogers et al. |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0077129 A1 | 3/2008 | Van Wyk et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0093804 A1 | 4/2009 | Newton |
| 2009/0138003 A1 | 5/2009 | DeVille et al. |
| 2009/0138013 A1 | 5/2009 | Thorne et al. |
| 2009/0192509 A1 | 7/2009 | Curtis |
| 2009/0248002 A1 | 10/2009 | Takashino et al. |
| 2010/0042096 A1 | 2/2010 | Ellman |
| 2010/0087814 A1 | 4/2010 | Desinger et al. |
| 2010/0137854 A1 | 6/2010 | Hosier |
| 2010/0179545 A1* | 7/2010 | Twomey ............ A61B 18/1445 606/51 |
| 2010/0228249 A1 | 9/2010 | Mohr |
| 2011/0045680 A1 | 2/2011 | Beller |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0319892 A1 | 12/2011 | Blomeyer |
| 2012/0022530 A1 | 1/2012 | Woodruff et al. |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0123405 A1 | 5/2012 | Moua et al. |
| 2012/0150165 A1 | 6/2012 | Conley |
| 2012/0202388 A1 | 8/2012 | Selig |
| 2013/0023874 A1 | 1/2013 | Lawes |
| 2013/0066317 A1 | 3/2013 | Evans et al. |
| 2013/0079762 A1 | 3/2013 | Twomey et al. |
| 2013/0178852 A1 | 7/2013 | Allen, IV et al. |
| 2013/0237982 A1 | 9/2013 | Rencher et al. |
| 2013/0296846 A1 | 11/2013 | Canady et al. |
| 2014/0100569 A1 | 4/2014 | Lawes et al. |
| 2014/0236202 A1 | 8/2014 | Palmer |
| 2014/0276795 A1 | 9/2014 | Batchelor et al. |
| 2014/0276799 A1 | 9/2014 | Batchelor et al. |
| 2015/0320485 A1 | 11/2015 | Batchelor et al. |

FOREIGN PATENT DOCUMENTS

| | | |
|---|---|---|
| CN | 102836006 | 12/2012 |
| EP | 0392548 A1 | 10/1994 |
| EP | 1089664 | 4/2001 |
| EP | 1530952 A1 | 5/2005 |
| EP | 1769765 A1 | 4/2007 |
| EP | 1810629 A2 | 7/2007 |
| EP | 1977706 A1 | 10/2008 |
| EP | 2403422 | 1/2012 |
| JP | H10-137259 A | 5/1998 |
| JP | H10-504485 A | 5/1998 |
| JP | 2000070280 A | 3/2000 |
| JP | 2001170070 A | 6/2001 |
| JP | 2004508875 A | 3/2004 |
| JP | 2005144192 A | 6/2005 |
| JP | 2005521465 A | 7/2005 |
| JP | 2009247893 A | 10/2009 |
| JP | 2012518490 A | 8/2012 |
| WO | 96/005776 A1 | 2/1996 |
| WO | 9966850 | 12/1999 |
| WO | 02/24089 A1 | 3/2002 |
| WO | 2006/122279 | 11/2006 |
| WO | 2007/002545 | 1/2007 |

(56) References Cited

FOREIGN PATENT DOCUMENTS

| WO | 2007093857 | 8/2007 |
|---|---|---|
| WO | 2010/101897 | 9/2010 |
| WO | 2012/053530 A | 4/2012 |
| WO | 2014/096815 A2 | 6/2014 |

OTHER PUBLICATIONS

Potentially related U.S. Appl. No. 14/589,515, filed Jan. 5, 2015.
Potentially related U.S. Appl. No. 14/829,725, filed Aug. 19, 2015.
Potentially related U.S. Appl. No. 14/830,069, filed Aug. 19, 2015.
Potentially related U.S. Appl. No. 14/830,255, filed Aug. 19, 2015.
International Search Report and Written Opinion for Application No. PCT/US2014/015916 dated May 12, 2014.
International Search Report and Written Opinion for Application No. PCT/US2014/015948 dated Apr. 30, 2014.
Potentially related U.S. Appl. No. 14/177,780, filed Feb. 11, 2014.
Potentially related U.S. Appl. No. 14/178,411, filed Feb. 12, 2014.
Potentially related U.S. Appl. No. 14/209,071, filed Mar. 13, 2014.
Potentially related U.S. Appl. No. 14/205,598, filed Mar. 12. 2014.
Potentially related U.S. Appl. No. 14/205,919, filed Mar. 12, 2014.
Potentially related to U.S. Appl. No. 14/206,010, filed Mar. 12, 2014.
Potentially related U.S. Appl. No. 14/210,535, filed Mar. 14. 2014.
Potentially related U.S. Appl. No. 14/210,741, filed Mar. 14, 2014.
Potentially related U.S. Appl. No. 14/211,042, filed Mar. 14, 2014.
Potentially related U.S. Appl. No. 14/178,577, filed Feb. 12, 2014.
315MHZ sliding remote cover, available at website : http://www.aliexpress.com/item/Sliding-Cover-Gate-Remote-Control-Duplicator-Adjustable-Frequency-Remote-Copy-100pCS-lot-Free-Shipping-by-DHL/566451354.html?tracelog=back_to_detail_a (accessed on Feb. 21, 2013).
Sliding Gate Remote Control Duplicator, available at website: http://www.aliexpress.com/item/315MHZ-sliding-cover-remote-controller-duplicating-remote-controller-sliding-gate-remote-garager-door-remote/491795542.html (accessed on Feb. 21, 2013).
Japanese Office Action dated Oct. 18, 2016, for Application No. 2016-500239.
European Patent Office Action dated Apr. 19, 2016, for Application No. 14706460.4.

\* cited by examiner

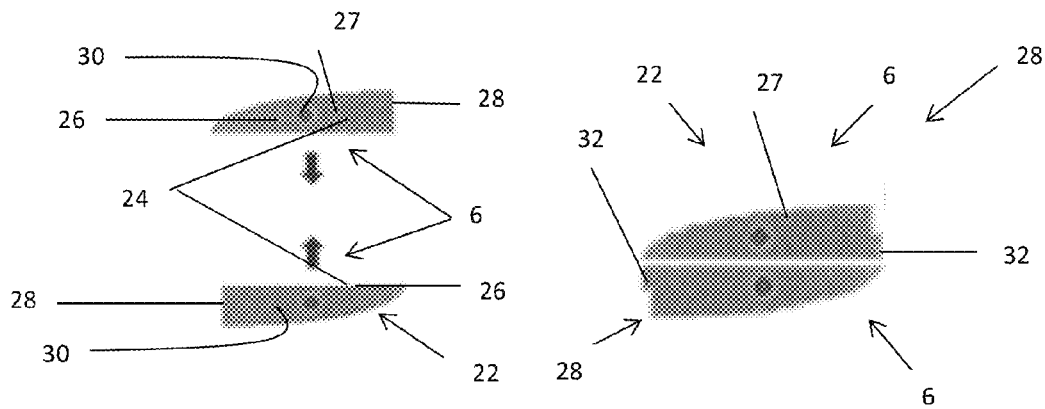
Fig – 9A  Fig – 9B
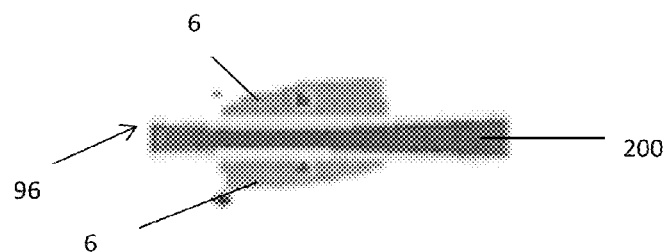
Fig – 9C
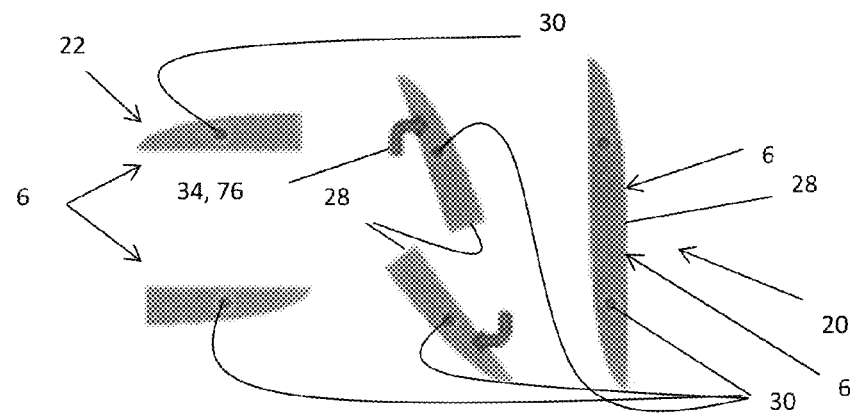
Fig – 10A  Fig – 10B  Fig – 10C

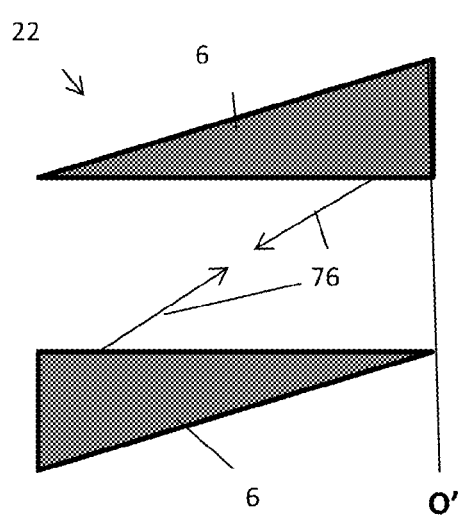
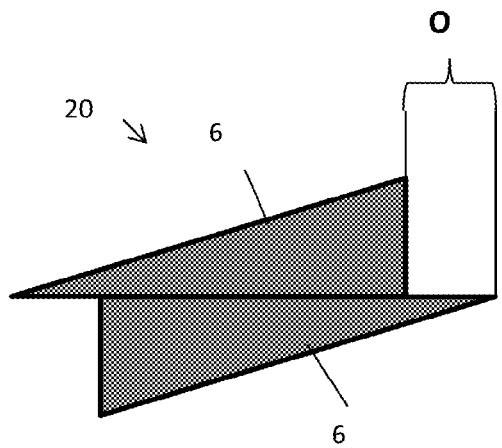
*Fig – 11A*  *Fig – 11B*
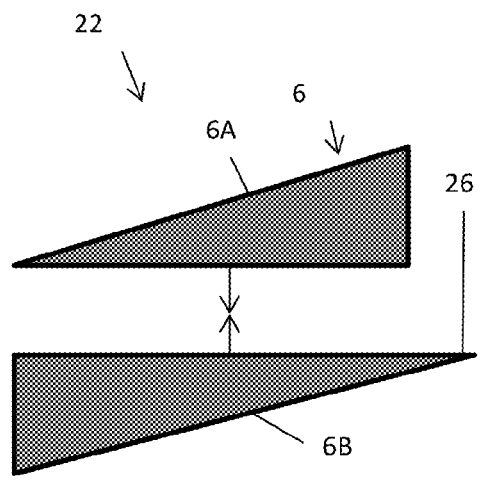
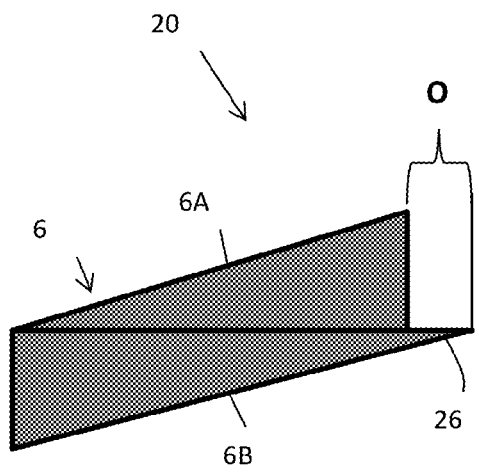
*Fig – 12A*  *Fig – 12B*

OFFSET FORCEPS

FIELD

The present teachings generally relate to forceps that include opposing working arms that are aligned in some configurations, offset or askew in all and/or some configurations, or a combination of both.

BACKGROUND

Typically, electrosurgical devices have stand-alone monopolar capabilities or bipolar capabilities. Thus, a surgeon before a procedure begins may select either a device with monopolar capabilities or a device with bipolar capabilities and the surgeon can use the device to apply either monopolar power or bipolar power. For example, if the surgeon selects a monopolar device and monopolar power is not desired for the surgical procedure the surgeon may use either the device that supplies monopolar power to perform the procedure or switch to a device with bipolar capabilities. Both of these devices may be used to perform the procedure, however, switching between devices and/or using a device that may be better suited for a different purpose may disturb the procedure flow, cause unnecessary delays in the procedure, and in some cases result in less than optimal energy sources being used.

Generally, electrosurgical devices are connected to a generator that produces a therapy signal and provides power to the electrosurgical device so that a therapy current is produced. However, the therapy currents that may be used are limited by the generator and thus if the generator is only capable of producing a single therapy current then only one therapy current can be applied through the electrosurgical device. Additionally, a generator may be capable of producing two therapy circuits, but the electrosurgical device may only be capable of controlling and applying a single therapy current. Thus, the electrosurgical device may only apply a single therapy current. Some attempts have been made to produce a device that includes both monopolar capabilities and bipolar capabilities in a single device.

Examples of some electrosurgical instruments may be found in U.S. Pat. Nos. 5,810,805; 5,902,301; 6,110.171; 6,464,704; and 6,726,686; and U.S. Patent Application Publication No. 2010/0087814 all of which are incorporated by reference herein for all purposes. It would be attractive to have an electrosurgical device that may be switched between a first electrosurgical configuration (e.g., a bipolar configuration) and a second electrosurgical configuration (e.g., a monopolar configuration) with one hand so that a user can easily perform a desired task without the need to disrupt the flow of a procedure. It would be attractive to have an electrosurgical device that may be used in open surgery as forceps and may be used for electrical cutting and/or hemostasis. What is needed is an electrosurgical device that can be switched between a gripping configuration and a cutting configuration without additional parts. It would be attractive to have an electrosurgical device that includes bipolar configuration and a monopolar configuration by mechanically reconfiguring forceps.

SUMMARY

The present teachings meet one or more of the present needs by providing: an electrosurgical device comprising: forceps including: (i) a first working arm having a contact surface and (ii) a second working arm having a contact surface; wherein the forceps has a first electrical configuration where the contact surface of the first working arm and the contact surface of the second working arm are substantially opposite each other so that the contact surfaces of the forceps can be used to grip an item between the working arms and so that the forceps is configured to deliver a first therapy current through the first working arm, the second working arm, or both; and wherein the forceps has second electrical configuration where the contact surface of the first working arm and the contact surface of the second working arm are askew relative to each other and an electrode edge is formed on at least one side of the forceps so that a second therapy current extends from the electrode edge.

Another possible embodiment of the present teachings comprises: an electrosurgical device comprising: forceps including: (i) a first working arm having a contact surface and (ii) a second working arm having a contact surface; wherein the forceps has a first configuration where the contact surface of the first working arm and the contact surface of the second working arm are substantially opposite each other so that the contact surfaces of the forceps can be used to grip an item between the working arms and so that the forceps is configured to deliver a first therapy current through the first working arm, the second working arm, or both; and wherein the forceps has a second configuration where the contact surface of the first working arm and the contact surface of the second working arm are askew relative to each other when the contact surfaces are brought into contact and an edge is formed on at least one side of the forceps so that the forceps is configured to cut tissue with the edge.

Yet another possible embodiment of the present teachings provides: an electrosurgical device comprising: forceps including: a first working arm having a contact surface and a second working arm having a contact surface; wherein the forceps have a bipolar position where the contact surface of the first working arm and the contact surface of the second working arm are substantially opposite each other so that the contact surfaces of the forceps can be used to grip an item between the working arms and so that a therapy current can be passed between the first working arm and the second working arm through the item; and wherein the forceps have a monopolar position where the contact surface of the first working arm and the contact surface of the second working arm are askew relative to each other and an electrode edge is formed on at least one side of the forceps so that the therapy current extends from the electrode edge.

The present teachings further provide: a method comprising: (a) providing an electrosurgical device including: (i) a first working arm and (ii) a second working arm; (b) moving the first working arm and the second working arm towards each other so that the first working arm and the second working arm are forceps and are configured in a bipolar configuration so that a therapy current can pass between the first working arm and the second working arm; and (c) configuring the first working arm and the second working so that the first working arm and the second working arm are askew relative to each other forming a monopolar configuration.

The teachings herein provide an electrosurgical device that may be switched between a first electrosurgical configuration (e.g., a bipolar configuration) and a second electrosurgical configuration (e.g., a monopolar configuration) with one hand so that a user can easily perform a desired task without the need to disrupt the flow of a procedure. The teachings herein provide an electrosurgical device that may be used in open surgery as forceps and may be used for electrical cutting and/or hemostasis. The teachings herein provide an electrosurgical device that can be switched between a gripping configuration and a cutting configuration without additional parts. The teachings herein provide an electrosurgical device that includes bipolar configuration and a monopolar configuration by mechanically reconfiguring forceps.

BRIEF DESCRIPTION OF THE DRAWINGS

FIG. 7A illustrates a working arm with a square body and pointed tip;

FIG. 7B illustrates a working arm with a flat body and pointed tip;

FIG. 7C illustrates a working arm with a square body and a pointed tip;

FIG. 7D illustrates a working arm with a rounded body and a blunt tip;

FIG. 9A illustrates a cross-sectional view of an alternative embodiment of the forceps being aligned and separated;

FIG. 9B illustrates a cross-sectional view of the forceps of FIG. 9B with the forceps being in contact and including a connection feature;

FIG. 9C illustrates a cross-sectional view of the forceps of FIG. 9A gripping tissue;

FIGS. 10A-10C illustrates a cross section of the forceps being reconfigured from bipolar position to a monopolar position.

FIG. 10A illustrates the forceps in the bipolar configuration;

FIG. 10B illustrates the working arms of the forceps rotating around axes;

FIG. 10C illustrates the forceps in the monopolar position;

FIG. 11A illustrates a cross-sectional view of forceps that are substantially aligned in the monopolar position;

FIG. 11B illustrates a cross-sectional view of the forceps when moved into a bipolar configuration and including an offset;

FIG. 12A illustrates a cross-sectional view of open forceps have different sized working arms;

FIG. 12B illustrates a cross-sectional view of closed forceps having different sized working arms;

DETAILED DESCRIPTION

Figure 1:
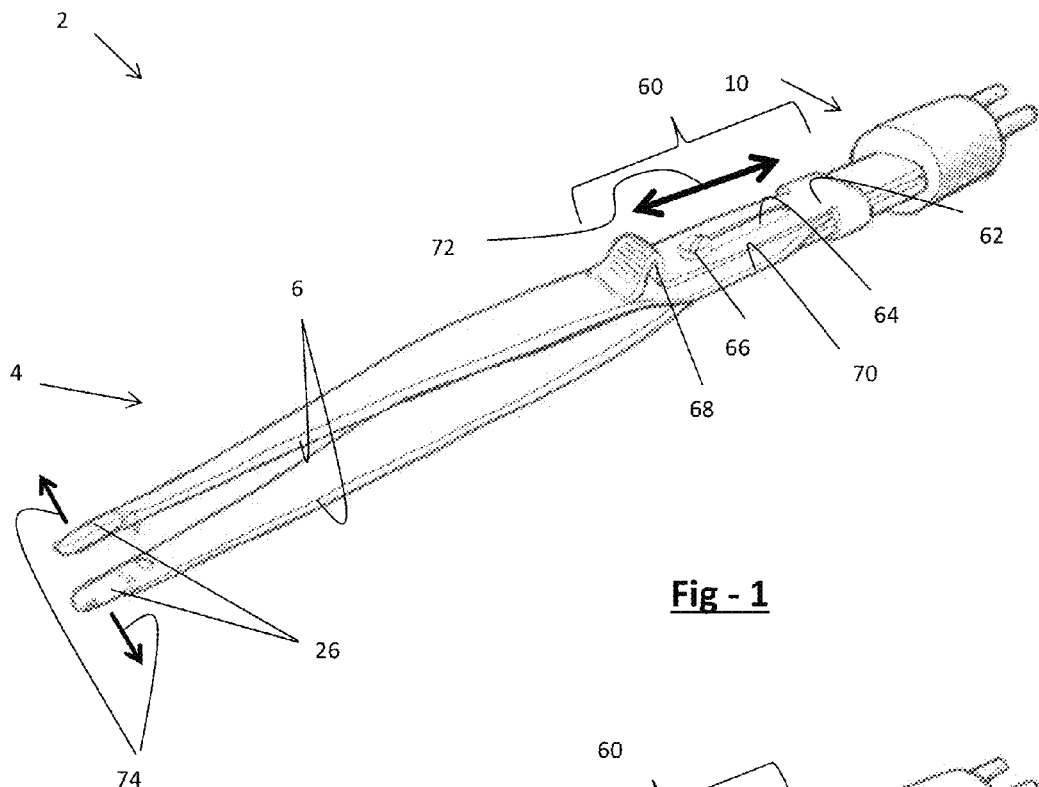
FIG. 1 illustrates an example of forceps of the teachings herein.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to an electrosurgical device. Preferably, the present teachings relate to an electrosurgical device and associated componentry that form an electrosurgical system. The electrosurgical system may be any system that includes one or more of the devices taught herein. Preferably, the electrical surgical system includes at least an electrosurgical device. More preferably, the electrosurgical system includes an electrosurgical device that is electrically connected to a generator. The electrosurgical system may include one or more handpieces as taught herein, one or more ground pads, one or more generators, one or more electrosurgical devices, one or more adjacent handpiece components, or a combination thereof and the teachings herein of each device which are incorporated into the electrosurgical system. The electrosurgical device may be any device that may be used by a surgeon to perform a surgical procedure. The electrosurgical device may be any device that may be switched between two or more configurations, two or more states, or both. For example, the electrosurgical device may be switched between a monopolar configuration, a bipolar configuration, or a combination of both. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate, fulgrate, electrocautery, or a combination thereof. The electrosurgical device may be any device that includes bipolar capabilities, monopolar capabilities, non-electrosurgical capabilities, or a combination thereof. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, a feature of interest, the like, or a combination thereof. In another example, the electrosurgical device may be used to cut, as a scalpel, or both. The electrosurgical device may include a handpiece and a generator. The electrosurgical device may have one or more therapy signals that extend between the handpiece and the generator.

The one or more therapy signals may be a signal, power, continuity, current, voltage, or a combination thereof. The one or more therapy signals may extend from the handpiece to the generator or vice versa. The one or more therapy signals may be formed by the handpiece, formed by the generator, or both. The electrosurgical therapy signals may be a therapy current. The electrosurgical therapy signals may provide a signal so that one or more therapy currents are produced and the therapy currents may be used for electrosurgery. The electrosurgical therapy signal may be a monopolar therapy signal, a bipolar therapy signal, or both. The electrosurgical therapy signal may be a monopolar generator signal, a bipolar generator signal, or both. The monopolar therapy signal may be any signal that has a voltage differential between a return port and an active port in the generator. The monopolar therapy signal may be any signal that when applied by the electrosurgical device extends: from one pole of an electrosurgical device to another pole located at a remote location, off of the electrosurgical device (e.g., from the handpiece to a location separate from the handpiece), off of the handpiece, from an edge electrode, or a combination thereof. The bipolar therapy signal may be any signal that has a voltage differential between two leads that are connected to the electrosurgical device, that are located in the generator, or both. The bipolar therapy signal may be any signal that when applied by the electrosurgical device extends from one component of a handpiece to another component of the handpiece (e.g., between two working arms, from two edge electrodes, or both). The therapy signal may be generated and conducted from the handpiece to the generator or vice versa.

The generator may be any device that supplies: power, voltage, a therapy current, control signals, an electrosurgical therapy signal, electrically reconfigures itself in response to a signal from the user and/or mechanical reconfiguration by the user, physically reconfigures in response to adjustments by the user, current, or a combination thereof. The generator may be any device that may be electrically connected to a handpiece to provide and/or receive electrosurgical therapy signals, power, therapy current, voltage, or a combination thereof. The generator may be capable of producing only a single therapy current. The single therapy current may be supplied to the electrosurgical device, and the mechanical configuration (e.g., the working arms being aligned, skewed, or a position therebetween) of the electrosurgical device may determine the type of therapy current applied (e.g., bipolar energy, monopolar energy, or both). The generator may be capable of producing two therapy currents. The generator may be capable of producing a plurality of therapy signals. The generator may include two or more power connections or three or more power connections. The power connections may be any port in the generator so that one or more power connectors of the handpiece may be plugged into so that power, control signals, therapy currents, voltage, or a combination thereof are supplied to the electrosurgical device. The generator may include one or more switches that may be switched between one or more of the power connections so that power, signals, or both may be selectively applied to the electrosurgical device based upon a desired configuration of the electrosurgical device. The generator may include a central processing unit (CPU). The CPU may electrically reconfigure the electrosurgical device without the need for physical reconfiguration. The CPU may be any device that provides power, signals, electrical reconfiguration, a switch between two or more therapy currents, a switch between two or more configurations, a switch between two or more therapy signals, or a combination thereof to the electrosurgical device so that the electrosurgical device may be used to perform a desired function as is discussed herein. The CPU may be used to switch the electrosurgical device between a first electrosurgical configuration, a second electrosurgical configuration, a third electrosurgical configuration, a monopolar configuration, a bipolar configuration, a non-electrosurgical configuration, or a combination thereof.

The first therapy current may be monopolar energy and/or monopolar current. Preferably, the first therapy current is bipolar energy and/or bipolar current. Bipolar energy may be any power source that during application extends from one pole of an electrosurgical device to another pole on the electrosurgical device. Stated another way, bipolar energy is energy that extends from one component on the forceps to another component on the forceps. Preferably, between two physically connected components of the forceps. For example, energy that extends between two separated working arms on the handpiece is bipolar energy. The first electrosurgical configuration may be deactivated and a second electrosurgical configuration activated.

The second electrosurgical configuration may provide a second therapy current. The second therapy current may be bipolar energy (e.g., bipolar current or bipolar power). Preferably, the second therapy current may be monopolar energy (e.g., monopolar current or monopolar power). Monopolar energy may be any power source that during application extends from one pole of an electrosurgical device to another pole, located at a remote location, off of the electrosurgical device, off the forceps, or a combination thereof. Stated another way, monopolar energy is energy that extends from one component of the forceps to a component that is not physically part of the forceps. For example, energy that extends from one or both working arms to a remote electrode (e.g., ground pad), which may be directly and/or indirectly electrically connected, is monopolar energy. The second electrosurgical configuration, the first electrosurgical configuration, or both may be reconfigured into a third electrosurgical configuration.

The third electrosurgical configuration may be any electrosurgical configuration, a non-electrosurgical configuration, or both so that the electrosurgical device may be used to perform a procedure. Preferably, the third electrosurgical configuration is a non-electrosurgical configuration. The non-electrosurgical configuration may be any configuration where power is not supplied to the forceps, the two or more working arms, or a combination thereof. The non-electrosurgical configuration may be used when the electrosurgical device is being used as forceps, tweezers, a clamp, Kelley hemostat forceps, scalpel, or a combination thereof. In the non-electrosurgical configuration the working arms may be mobile. Preferably, the working arms are immobilized in the non-electrosurgical configuration. In the non-electrosurgical configuration the therapy current may not pass through the forceps, the working arms, the electrosurgical device, or a combination thereof.

The therapy current that extends through the forceps may be effected by a signal and/or current from the generator; a forceps position (e.g., first position, second position, third position, etc. . . . ); or a combination thereof. For example, the therapy current may be monopolar energy when the working arms are in the second position. However, the therapy current may be bipolar energy when the working arms are in the second position. In another example, the therapy current may be a bipolar energy when the electrosurgical is in the first position. The first electrosurgical configuration, second electrosurgical configuration, and third electrosurgical configuration may be any configuration that may perform one or more of the functions as discussed herein for the monopolar configuration, bipolar configuration, and non-electrosurgical configuration and each of those functions are incorporated herein. Preferably, as discussed herein the first electrosurgical configuration is a bipolar configuration, the second electrosurgical configuration is a monopolar configuration, and the third electrosurgical configuration is a non-electrosurgical configuration.

The forceps when in a monopolar configuration may supply power through a handpiece component (e.g., a pair of connected immobilized working arms) and a return electrode (e.g., that may be located at another location outside of the hand held portion of the electrosurgical device), through a handpiece component and an adjacent handpiece component, or both. The monopolar configuration may be any configuration where the electrosurgical device may be used to apply monopolar power. The monopolar configuration may be used to cut tissue, coagulate blood and/or fluids, electrical cutting, hemostasis, apply power to a large area, or a combination thereof. The monopolar configuration may be used to heat a specific area, heat an object between both electrodes, in contact with both electrodes, or a combination thereof. The monopolar electrosurgery may be used for less delicate procedures, less localized electrosurgery, or both when compared to bipolar electrosurgery.

The device when in a bipolar configuration may supply power from one portion of the device to a second portion of the device so that the return path for the power is relatively short when compared to the monopolar configuration. The bipolar configuration may be any configuration where the electrosurgical device may be used to apply bipolar power. The forceps when in the bipolar configuration may supply power between two localized handpiece components such as two working arms. The bipolar configuration may be used to coagulate, for hemostasis, cutting, fulguration, or a combination thereof. When in the bipolar configuration, the electrosurgical device may include two opposing working arms. The two opposing working arms may be configured as forceps.

The forceps may be any forceps that may be used to grip, hold, squeeze, or a combination thereof one or more objects. The forceps may include one or more finger grips (i.e., configured like scissors) that may be used to move the forceps so that they may be used to grip one or more objects. Preferably, the forceps may be free of finger grips and be actuated by direct pressure being applied to opposing sides of the forceps so that the forceps close and grip an object. More preferably, the forces are closed by direct pressure being applied to a back of a pair of working arms. The forceps include at least two working arms.

The working arms may be any part of the electrosurgical device that may be used to grip, hold, squeeze, or a combination thereof an object when the object is between the two or more opposing working arms. The working arms may include one or more gripping features that may assist in gripping, holding, squeezing, or a combination thereof an object. The working arms may be movable between two or more positions. Preferably, the working arms are movable between at least a first position and a second position. For example, the working arms may be movable between a bipolar configuration (e.g., first position) and a monopolar configuration (e.g., second position). In another example, the working arms may be movable between an opposing position and an askew position. The working arms in the first position may be electrically off, energized, one working arm may be energized, used as tweezers, or a combination thereof. The working arms in the second position may be electrically off, one or both of the working arms may be electrically disconnected, one or both of the working arms may be electrically connected, one working arm may be shorted by the other working arm, or a combination thereof. More preferably, in the second position one or both of the working arms are immobilized so that the working arms cannot be used a forceps. The working arms may be longitudinally static (e.g., along a length of the working arms) and moveable relative to each other (e.g., both laterally and rotationally). The working arms may be laterally moveable (e.g., at substantially a right angle to the longitudinal axis; however, this angle may change as one or both of the working arms are moved) and may be moveable relative to each other so that a gripping force may be created. The working arms may be rotatable around a longitudinal axis, rotational axis, or both individually, simultaneously, or both. The working arms may include a body and a tip, electrode edge, or both.

The body may be any part of the working arm that assists in creating a gripping force, in connecting two opposing working arms together, or both. The body may be a majority (i.e., 60 percent or more, 70 percent or more, or even 80 percent or more) of a gripping region of a working arm. A connection region may be located between the two opposing bodies of the working arms so that substantially all of the connection regions of the body are in contact when the working arms are in a gripping configuration, a skewed configuration, or both. The body portion may be any part that grips a feature of interest, is connected to a tip, provides a connection point for a tip, or a combination thereof. Each body may include an axis that the working arms rotate about. The body may be partially and/or entirely made of an electrically conductive material, an insulative material, or both. The body may include one or more wires, one or more power connectors, or both that may extend through the body. The body may be any size and shape so that the body portion supports a tip, has a gripping portion, conducts electricity, may be used as forceps, or a combination thereof. The body may have a cross section that is square, rectangular, half-circle, half-oval, oblong, geometric (i.e., a known geometric shape), symmetrical, asymmetrical, includes steps, is linear, includes a bulbous portion, or a combination thereof. The body may include a contact surface, a contact region, a connection region, or a combination thereof.

The connection region may be any part of the body, the working arms, or both that secures the working arms together, the body portions together, or both. The connection region may be a region where two opposing working arms contact each other. The connection region may be a region where two opposing working arms lock together. The connection regions when in contact may prevent the working arms from moving relative to each other (e.g., rotating). The connection regions may be smooth, complementary to an opposing connection region, a tongue and groove, interfitted pieces, a projection and a recess, opposing projections, opposing recesses, or a combination thereof. The connection regions of the two working arms may be in contact in the bipolar configuration, monopolar configuration, non-electrosurgical configuration, or both. The connection regions of the two working arms may be in contact only in the monopolar configuration. The connection region may be located on an opposite end of the body, the working arms, or both as a tip, a tip region, or both. For example, the ends may be substantially parallel to a gripping direction when the working arms are moved towards each other. Preferably, the tip extends from one side of a body and the connection region extends from an opposing side of the body.

A tip region, a tip, or both of the working arms may extend beyond a body when the working arms are in the skewed configuration. The tip region, tip, or both may function to deliver current to a location of interest, to assist in gripping an object of interest, assist in moving an object of interest, form a cutting surface, or a combination thereof. The tip, tip region, or both may be an edge and/or side of the working arms. The tip and/or tip region may be an edge of the working arms that form a point in a cross section, a non-blunt surface, or both. The tip region may include a portion that is configured to assist in facilitating gripping, holding, squeezing, or a combination thereof. The tip region may be configured and/or moved to one or more electrosurgical configurations (e.g., a monopolar configuration, bipolar configuration, non-electrosurgical, or a combination thereof). The tip region may include teeth, serrations, mouse teeth, be free of teeth (i.e., smooth), or a combination thereof. The tip region may be fully and/or partially insulated. Preferably, the tip region includes insulation on the non-contact portions of the working arms so that electrosurgical energy is not transferred through incidental contact. The tip may extend beyond a body of the working arms so that the tip is exposed and may be used for cutting, applying a therapy current, or both. The tip, tip region, or both may be any size and shape so that the tip may be used for cutting, applying a therapy current, or both. The tip may be blunt, sharp, serrated, smooth, rounded, angled, smaller than the body portion, shorter than the body portion, longer than the body portion, thinner than the body portion, of a combination thereof. The tip may not be able to cut tissue (e.g., be blunt). Preferably, the tip region may be an edge electrode, may form an edge electrode, may be part of an edge electrode, or a combination thereof.

The edge electrode may be any part of the forceps, the working arms, or both that may create a cutting edge, an edge for applying a therapy current, or both. The edge may function as a mechanical blade (e.g., a blade, scalpel, surgical scalpel, or a combination thereof). The edge electrode may be a point (when viewed in a cross-section) and/or plane for applying power, a point and/or plane for mechanical cutting, a portion of one working arm that extends past an opposing working arm and/or opposing body portion in one or more configurations, or a combination thereof. The edge electrode may be any part of the working arms that extends beyond an opposing working arm and/or body. The edge electrode may be an active portion and/or include an active portion. The edge electrode may include an active portion and an inactive portion (i.e., an insulated portion).

The active portion may be any portion of the device that may be used to apply power, a therapy current, or both. The active portion may be the same portion as the contact regions of the forceps. Thus, for example, when tissue is grasped between the contact portions of the forceps, power may be supplied to the tissue through this contact portion. The active portion of the working arms preferably is between the two opposing working arms, the active portion during a monopolar extends from a side and/or edge of one or both working arms, or both. The only exposed active portion may be found at the edge electrode, the tip, a tip region, a contact region, a contact surface, or a combination thereof. Preferably, at least the edge electrode includes an exposed active portion. The active portions may be substantially surrounded by inactive portions or portions that are insulated.

The inactive portion may be any portion that does not supply power, that is insulated, or both. The inactive portion may be any portion that may prevent a transfer power through incidental contact and thus are insulated so that an incidental transfer of power does not occur. For example, an outside of the working arms may be coated with an insulating material so that if the working arms accidentally contact tissue proximate to the tissue of interest the proximate tissue is not subjected to a transfer of power. The body may be partially, substantially entirely, or entirely covered with inactive material, be inactive, or both. The inactive portion and the active portion may be made of different materials, coated with different materials, or both.

The working arms may be made of any material that may be used to grip, hold, squeeze, or a combination thereof and provide monopolar power, bipolar power, a therapy current, a gripping force, or a combination thereof to a desired location. The body and/or base of the working arms may be made of one material and the tip region of each working arm may include, be coated with, or both one or more materials that may be insulating, a higher thermal conductivity than the body and/or base material, a lower thermal conductivity than the body and/or base material, or a combination thereof. Each of the working arms may include a material with a thermal conductivity and the thermal conductivity of the working arms may be the same, one working arm may be higher than the other working arm, or both. The one or more working arms may include one or more materials along the length of the working arm. For example, the working arms may be entirely made of stainless steel. Preferably, each working arm includes two or more materials. For example, the working arms may have a base material of stainless steel and the working arms may be coated with an insulating material such as silicone or polytetrafluoroethylene (PTFE). The working arms may include any material that is safe for use in a surgical procedure, and preferably and electrosurgical procedure. The working arms may include metals, plastics, a polymer, an elastomer, gold, silver, copper, titanium, aluminum, iron based metals, stainless steel, silicone, polytetrafluoroethylene (PTFE), insulating polymers, rubber, or a combination thereof. Preferably, each working arm is substantially coated with an insulating material except for a contact region between the two working arms where the working arms contact each other, a tip, an edge electrode, or a combination thereof. The working arms may be coated in regions where the user contacts the working arms. The working arms may have an active portion, a passive portion, an inactive portion, or a combination thereof. For example, the active portion may be the metal that extends through the working arms and is used to provide monopolar energy, bipolar energy, gripping capabilities, holding capabilities, squeezing capabilities, or a combination thereof. All or a portion of the active portion may be covered, protected from conducting power, or both when the working arms are immobilized, askew, in a neutral position, or a combination thereof.

The two or more working arms may be immobilized by an immobilization feature and/or immobilization device. The immobilization feature and/or immobilization device may be any feature that immobilizes one or both of the working arms so that the forceps are disabled in the monopolar configuration (e.g., the working arms are prevented from laterally moving and/or rotationally moving). The immobilization features and/or immobilization device may be part of the arms, part of a housing, all or a part of a skewing device, or a combination thereof. The immobilization features and/or immobilization device may be a connection region, the skewing device, or both as discussed herein.

The skewing device may be any device and/or part of the forceps that skews the working arms relative to each other, moves the working arms so that they are askew relative to each other, or both. The skewing device may laterally skew the working arms, rotationally skew the working arms, diagonally skew the working arms, or a combination thereof. The skewing device may be any device that may offset the working arms relative to each other, the tips of the working arms relative to each other, the contact surfaces relative to each other, or a combination thereof. The skewing device may move along a longitudinal axis of the working arms, may rotate the working arms around a rotational axis of the working arms, or both. The skewing device may be in communication with one or both of the working arms, may move relative to one or both of the working arms, or both. The skewing device may extend substantially around both of the working arms an move longitudinally along the working arms so that the working arms are moved laterally relative and/or rotationally to each other. The skewing device may connect to one or both working arms so that the skewing device moves the working arms relative to each other. The skewing device may connect one or both sides of one or more working arms. The skewing device may be a sleeve that extends around both working arms, "C" shaped and in contact with both working arms, may extend between the working arms and be two back to back "C" shapes, or a combination thereof. The skewing device may connection a region of two opposing working arms together. The skewing device may lock in place, may prevent the working arms from being partially skewed, or both. The skewing device may include a pathway.

The pathway may be any part of the skewing device that guides the skewing device along the forceps, the working arms, or both. The pathway may dictate the amount of skewing, the direction of skewing, or both. Depending on the amount of skewing desired different pathways may be chosen so that the working arms may be more or less askew relative to each other. For example, the pathway may include a small, medium, and large path way. The pathway may be a through hole that extends through a portion of the skewing device. A pathway may be located on one or both sides of the skewing device. For example, one pathway may be located proximate to one working arm and an opposing pathway may be located proximate to the second working arm. If more than one pathway is present the pathways may cause the working arms to skew in opposite directions so that each working arm moves half of the distance to an askew state. The pathway may be a groove, a hole, a track, a series of holes, a track, a recess, a series of recesses, or a combination thereof. The pathway may extend along all or a portion of a length of the skewing device. The pathway may be planar, arcuate, curved, stepped, include a change of direction, be linear, non-linear, "S" shaped, "Z" shaped, "H" shaped, "Y" shaped, "W" shaped, include two or more parallel portions with an angled segment connecting them, helical, or a combination thereof. The pathway may guide the skewing device as the skewing device is moved along a length of the forceps, one of the working arms, both of the working arms, or a combination thereof. The pathway may receive a pin, move along a pin, or both The pin may be any device that assists in controlling a direction of movement of the skewing device, the amount of skewing of the arms relative to each other, or both. The pin may bias the skewing device. The pin may guide the skewing device, work in conjunction with the pathway to skew the working arms, or both. The pin may connect to one or both of the working arms and as the skewing device is extended longitudinally along one or both of the working arms the skewing device may apply a lateral force, a rotational force, or both to one or both of the working arms so that the working arms are moved from a neutral state to an askew position (e.g., moved so that the working arms are askew relative to each other). Preferably, the pin is connected to one of the working arms so that the skewing device skews the working arm with the pin and the working arm without the pin remains static. The pin may surround an outer portion of the skewing device and guide the skewing device as the skewing device is longitudinally moved. The pin may be located on the top, bottom, edge, side, or a combination thereof of one or both of the working arms. The number of pins may be commensurate with the number of pathways. Each working arm may include a pin. The pin may be a deflector that deflects (i.e., skews) one or both working arms.

The deflector may be any feature that moves one or both of the working arms relative to each other. The deflector may work in conjunction with the skewing device to bias one or both of the working arms. The deflector may laterally move, rotationally move, diagonally move (i.e., skew) one or both of the working arms relative to each other. The deflector may be part of the skewing device. Preferably, the deflector is part of one or both of the working arms. More preferably, the deflector is in communication with the skewing device and as the skewing device moves along the deflector one or both of the working arms are skewed. The deflector may extend from a top of a working arm, however, preferably the deflector extends from a side of a working arm. The deflector may be linear, angled, tapered, have a ramp shape, gradually become thicker, gradually become thinner, widen one or both of the working arms, be helically shaped, or a combination thereof. Preferably, the deflector extends from one or both of the working arms at an angle so that as the skewing device is extended over the deflector the deflector gradually skews the working arms relative to each other while simultaneously reducing movement of the working arms until the working arms are immobilized. For example, each working arm may include a deflector and the deflector may have a ramp shape so that as the skewing device is slid over the deflectors the skewing device compresses working arms via the deflector and the working arms are moved so that the working arms are askew relative to each other. The skewing device may be moved over the deflector by a bias feature.

The bias feature may be any device that may move and/or be used to move the skewing device, the deflectors, or both so that the working arms are skewed relative to each other. The bias feature may be any feature that a user applies a force to move the working arms relative to each other. The bias feature may be a raised feature, a lever, a series of ribs, a knob, a wheel, a device that provides a mechanical advantage and/or torque, or a combination thereof. The bias feature may be any feature that assists a user in skewing the working arms relative to each other. The bias feature may assist in moving the skewing device, locking the skewing device in place, or both. The bias feature may assist in creating an askew movement.

An askew movement is any movement where the working arms are moved from a position of being generally aligned to a position where at least a portion of one of the working arms is offset relative to each other or vice versa. Askew movement may be a rotation of one or both working arms around an axis, diagonal movement of one or both arms, lateral movement of one or both arm, or a combination thereof. Askew movement may be any movement where the working arms are moved from being generally aligned to being generally offset (i.e., askew) or vice versa. Askew movement may be a scissor like movement of the working arms relative to each other, movement of the working arms so that a tip extends beyond an opposing working arm, movement of the working arms so that all or a portion of a contact surface is not opposed by a contact surface of an opposing working arm, movement of a working arm so that a portion of one or both working arms extends beyond a body portion of an opposing working arm, or a combination thereof. The askew movement may be any movement of the working arms that causes the working arms to move in a skewing direction so that the working arms are moved from being askew to being generally aligned or vice versa.

Askew may be any angle formed between the working arms, the contact surface of the working arms, the edge electrode, or a combination thereof. Askew may be a lateral offset, a rotational offset, a diagonal offset, or a combination thereof of the working arms, a contact surface of the working arms, an edge electrode of the working arms, or a combination thereof. The working arms may move so that the working arms are askew in more than one way. For example the working arms may both laterally move and rotationally move. Lateral offset may be any offset where a portion of at least one working arm (e.g., a tip) extends beyond a portion of an opposing working arm, or vice versa. A lateral offset may exist when one or both working arms are laterally moved 1 mm or more, 2 mm or more, 3 mm or more relative to each other so that an amount of the working arm over hanging the opposing working arm corresponds to the distance of lateral movement. The lateral movement may result in the working arms being pivoted away from each other so that an angle results between the two working arms. The angle may be any angle so that the working arms are askew relative to each other. The angle may be about 5 degrees or more, about 10 degrees or more, or about 15 degrees or more. The angle may be about 75 degrees or less, about 60 degrees or less, about 45 degrees or less, or even about 30 degrees or less. The working arms may be askew so that the working arms are rotationally offset relative to each other.

A rotational offset and/or rotationally askew may be any movement and/or configuration where one or both of the working arms are rotated about an axis so that the edge electrodes, contact surfaces, or both are moved out of alignment, to an angle relative to each other, facing in opposing directions, or a combination thereof. Rotationally askew may result in the contact surfaces being located on opposing sides of the working arms (e.g., facing in opposing directions). A rotational movement may move one or more connection regions so that the connection regions are aligned relative to each other and the working arms may be connected together. Rotational movement may result in the working arms being rotationally askew and/or rotationally offset relative to each other. A rotational offset may be the result of a rotational movement that moves the working arms relative to each other. Rotationally askew may result one or both working arms rotating by about 45 degrees or more, preferably about 75 degrees or more, more preferably about 90 degrees or more, about 270 degrees or less, or about 180 degrees or less. The working arms may both rotationally move and laterally move and/or diagonally move so that a rotational offset and lateral offset and/or diagonal offset are achieved.

A diagonal offset and/or diagonally askew may be any movement and/or configuration where one or both working arms are moved at an angle relative to each other so that an offset is formed. Preferably, a diagonal offset occurs when the working arms are closing to create a gripping force and the working arms simultaneously become offset relative to each other. For example, the working arms may move both in a scissor like movement and towards each other to create a gripping force. Diagonally askew and/or diagonally offset may be the result of movement in the skewing direction.

The skewing direction may be any direction that results in the working arms being askew relative to each other. For example, the skewing direction may be lateral movement such as like scissors so that the working arms are offset relative to each other. In another example, the skewing direction may be rotation of the working arms so that contact surface of the working arms are moved from being generally opposed to being offset relative to each other (i.e., rotationally offset, not aligned relative to each other, or both). Movement of the working arms in the skewing direction and/or a skewing movement may cause mechanical reconfiguration, electrical reconfiguration, or both of one or more circuits of the forceps so that application of power through the forceps is changed.

The circuit may have a switch that switches between a bipolar configuration (e.g., first configuration), a monopolar configuration (e.g., second configuration), or both. The switch may activate one or more of the working arms and deactivate a remote electrode (e.g., ground pad or return pad) or vice versa; activate one or more working arms and deactivate one or more working arms or vice versa; deactivate one working arms and electrically connect the two working arms to a single power source; deactivate the ground pad; deactivate all of the working arms; or a combination thereof. The working arms may be connected to an alternating current power source, a direct current power source, or both. Preferably, the monopolar electrodes, the bipolar electrodes, or both are connected to an alternating current power source. A first working arm, a second working arm, or both may be indirectly connected to a power source through a handpiece, the opposing working arm, or both.

As discussed herein various circuits may be created by electrically reconfiguring one or more components of the electrosurgical device, physically configuring one or more components of the electrosurgical device, or both. During use one or more switches may be opened and/or closed so that one or more open circuits, one or more closed circuits, or both may be formed. For example, a working arm may be skewed so that a connection is formed between the working arm and a power source so that a circuit is completed, and an open circuit may be created between the power source and the working arms so that one of working arms are not powered and a ground pad is powered. The circuits may be configured so that a circuit is created between two or more components and the electrosurgical device may be used for a desired type of electrosurgery. The electrosurgical instrument may be configured so that power flows from one or more working arms to, another working arms, the ground pad, or a combination of both. The electrosurgical device may be configured with one or more power connectors, preferably two or more power connectors, and more preferably three or more power connectors. Each of the power connectors may be connected to one or more components, two or more components, or even three or more components. Each power connector may be switched between one or more components, two or more components, or even three or more components.

A method of switching the electrosurgical device between a bipolar configuration (i.e., first configuration), a monopolar configuration (i.e., second configuration), a non-electrosurgical configuration (i.e., third configuration), or a combination thereof. The method may include one or more of the steps discussed herein in virtually any order. The method may include a step of skewing one or both of the working arms relative to each other. The method may include a step of rotationally skewing one or both working arms, laterally skewing one or both working arms, diagonally skewing one or both working arms, or a combination thereof A skewing device may be advanced, retracted, or both. A force may be applied to a deflector, removed from a deflector, or both. An offset may be created between the working arms, a tip may be extended beyond a body portion of an opposing working arm, contact surfaces may be partially and/or fully out of overlap, or a combination thereof. The method may include a step of applying monopolar power and then immediately subsequently applying bipolar power or vice versa. The method may include a step of cutting in a non-electrosurgical configuration and then applying either monopolar power or bipolar power to coagulate, cauterize, or both without a step of changing instruments. The method may include a step of cutting in a monopolar configuration and then coagulating, cauterizing, or both using bipolar energy without a step of changing instruments.

FIG. 1 illustrates an example of an electrosurgical device 2 having a power connector 10 so that power can be transmitted through the electrosurgical device 2. The electrosurgical device 2 includes forceps 4 having a pair of working arms 6. The working arms 6 each include a tip 26 where power is transmitted through and/or gripping performed. The forceps 4 as illustrated have a skewing region 60 at a base proximate to the power connector 10. The skewing region 60 includes a skewing device 62 that skews the tips 26 of each working arm relative to each other in the directions 74. The skewing device 62 is moved along the electrosurgical device 2 in the direction 72 by a user pressing on the bias feature 68. As a force is applied to the bias feature 68 the skewing device 62 is moved along the skewing region 60 so that the skewing device 62 creates a force on the deflectors 70 forcing the deflector to deflect into the skewing device 62, which deflects the respective working arms 6 in the direction 74. As a force is applied to the bias feature 68 a pathway 64 in the skewing device 62 travels along a pin 66 that guides the skewing device 62 so that the working arms 6 are moved between an askew position and a forceps position.

Figure 2:
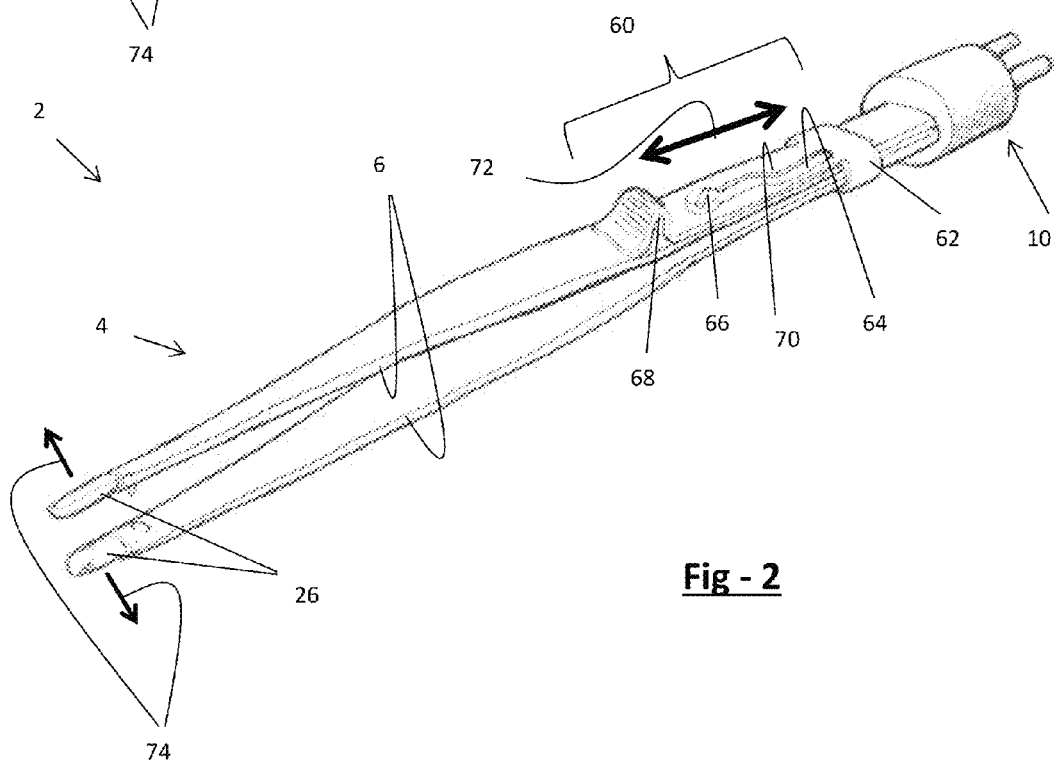
FIG. 2 illustrates another example of forceps of the teachings herein.

FIG. 2 illustrates another example of an electrosurgical device 2 having a power connector 10 so that power can be transmitted through the electrosurgical device 2. The electrosurgical device 2 includes forceps 4 having a pair of working arms 6. The working arms 6 each include a tip 26 where power is transmitted through and/or gripping performed. The forceps 4 as illustrated having a skewing region 60 at a base proximate to the power connector 10. The skewing region 60 includes a skewing device 62 that skews the tips 26 of the working arms 6 in the directions 74. The skewing device 62 is moved along the electrosurgical device 2 in the direction 72 by a user pressing on the bias feature 68. As a force is applied to the bias feature 68 the skewing device 62 moves along a pin 66 that is located within a pathway 64 that guides the skewing device 62. As the skewing device 62 moves along the pathway 64 the pin 66 is moved into contact with a deflector 70 that deflects the working arms 6 in the directions 74 so that the working arms are moved from a forceps position to an askew position. As shown the pathway 64 has a deflector 70 in the pathway 64 so that the deflector during movement of the skewing device 62 applies a force to the working arms 6 so that the working arms 6 are moved to an askew position.

Figure 3:
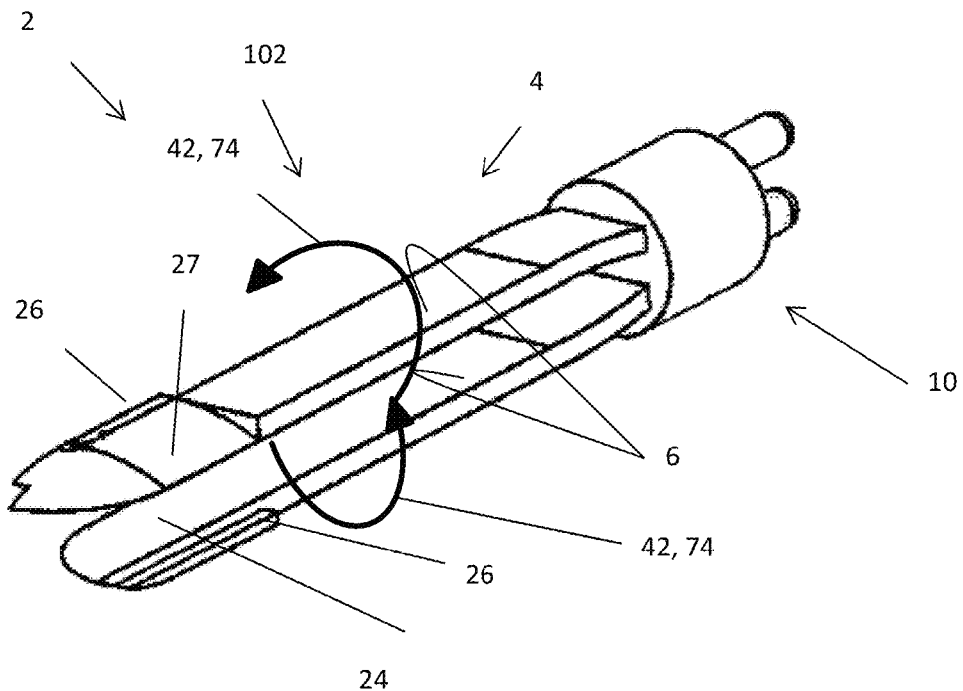
FIG. 3 illustrates an example of forceps with rotatable working arms of the teachings herein.

FIG. 3 illustrates another example of an electrosurgical device 2. The electrosurgical device 2 includes forceps 4 including a pair of working arms 6 connected to a power connector 10. The working arms 6 include a contact surface 24, a body 27, and a tip 26. The working arms 6 are each rotatable in the direction 42 (i.e., an askew movement) from a bipolar configuration 102 to a monopolar configuration (the conversion of which is shown as an example in FIGS. 10A-10C).

Figure 4:
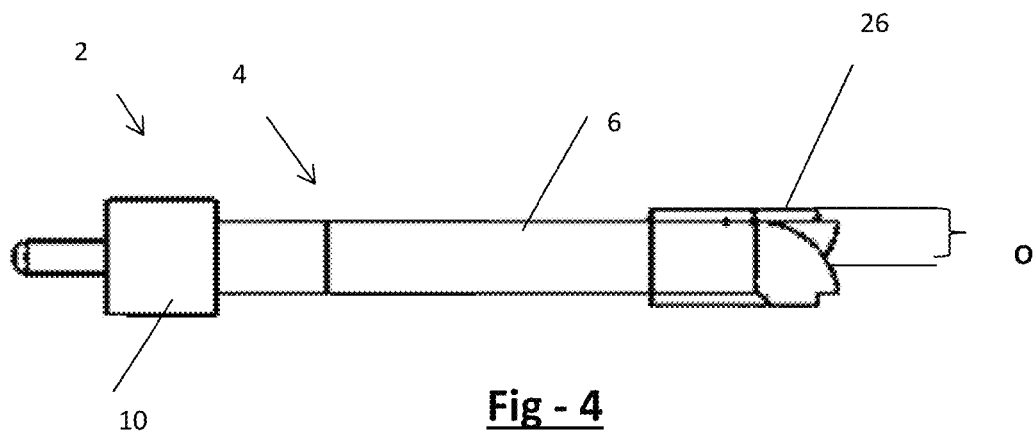
FIG. 4 illustrates a top view of the forceps of FIG. 3.

FIG. 4 illustrates a top view of the electrosurgical device 2 and forceps 4 of FIG. 3. As shown, the working arms 6 extend from the power connector 10. Each working arms 6 include a tip portion 26. The tips 26 of the working arms 6 are offset a distance (O) relative to each other.

Figure 5A:
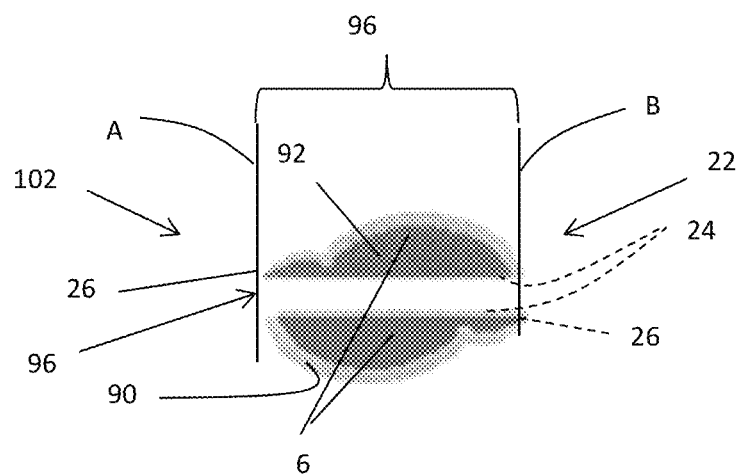
FIG. 5A illustrates a cross-sectional view of one example of a pair of forceps tips when the tips are spaced apart and aligned.

FIG. 5A illustrates a cross-sectional view of working arms 6 of an electrosurgical device (not shown) in a bipolar configuration 102 with the pair of working arms 6 being separated. The pair of working arms 6 are in a bipolar position 22 so that a contact surface 24 of each working arm 6 are directly opposing each other between line A and line B. A contact region 96 is formed between the working arms 6 and the working arms 6 are movable into contact so that the length of the respective contact surfaces 24 contact each other. Each of the working arms 6 include a tip 26 that forms an electrode edge that extends to a point and the tips 26 of the working arms face in opposing directions (although they may face in the same direction). The working arms 6 are made of a material with high thermal property 92 and the material with the high thermal property 92 is covered by a material with insulating thermal properties 90 that ends at the contact regions so that power may pass between the working arms 6 in the contact region 96.

FIG. 58B illustrates a cross-sectional view of the pair of working arms 6 moved into contact so that the ends 25 of the working arms align along line A and line B. In the contact region 96, the contact surfaces 24 are contiguous along the entire length.

Figure 5B:
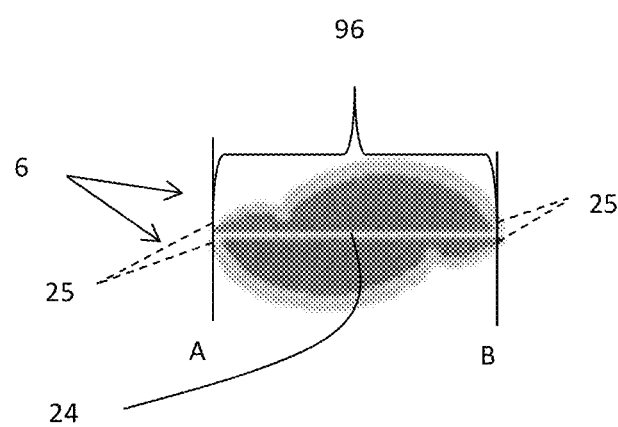
FIG. 5B illustrates the forceps tips of FIG. 5A askew and aligned.
Figure 5C:
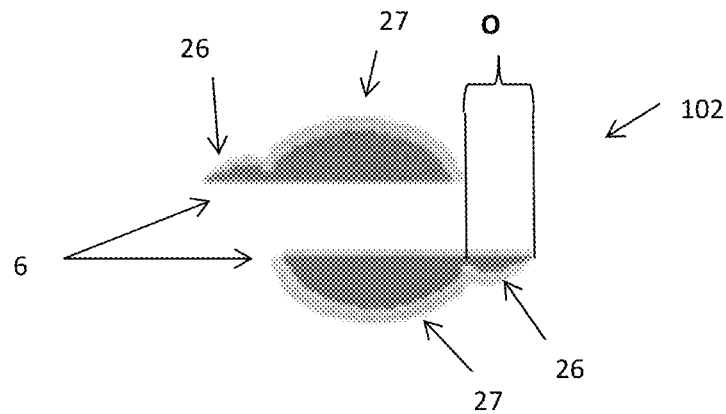
FIG. 5C illustrates the forceps tips of FIG. 5A askew when the forceps tips are spaced apart.

FIG. 5C illustrates a cross-sectional view of a bipolar configuration 102 with the working arms 6 separated and skewed so that an offset (O) is present and the tips 26 extend beyond the body 27 of the opposing working arm 6.

Figure 5D:
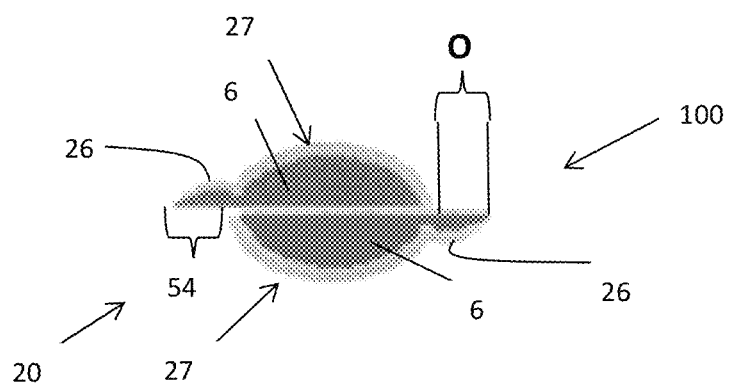
FIG. 5D illustrates the forceps tips of FIG. 5A in an offset configuration when the forceps tips are in contact.

FIG. 5D illustrates a cross-sectional view of the working arms 6 when the working arms 6 are moved to a monopolar position 20 when the electrosurgical device (not shown) is changed to a monopolar configuration 100. In the monopolar configuration 100, the working arms 6 are askew relative to each other and laterally offset a distance (O) so that the tips 26 extend beyond a body 27 of the opposing working arm 6 forming an edge electrode 54.

Figure 5E:
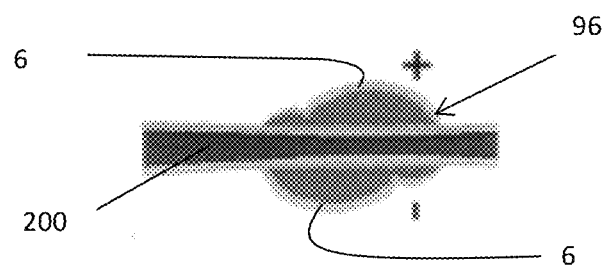
FIG. 5E illustrate the forceps tips of FIG. 5B gripping tissue therebetween.

FIG. 5E illustrates tissue 200 located in the contact region 96 between the working arms 6 when the working arms 6 are moved from the position of FIG. 5A towards the position of FIG. 5B. During application of power, power extends from one working arm 6 through the tissue 200 to the opposing working arm 6.

Figure 5F:
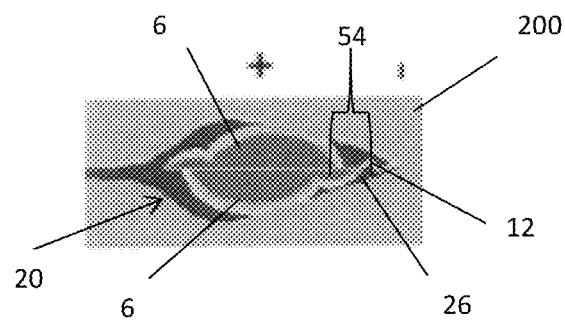
FIG. 5F illustrate the forceps tips of FIG. 5D cutting tissue.

FIG. 5F illustrates the working arms 6 in the monopolar position 20 as shown in FIG. 5D. The tips 26 form an edge electrode 54 and the edge electrode 54 is contacting tissue 200 so that power 12 is transferred from the tip to the tissue 200 for performing a predetermined procedure on the tissue 200.

Figure 6A:
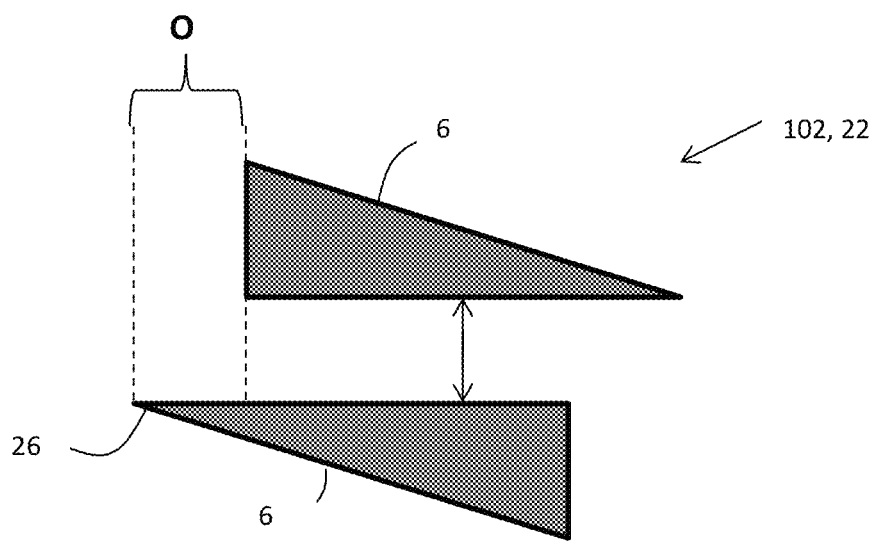
FIG. 6A illustrates a cross-sectional view of forceps tips that are askew in the forceps configuration.

FIG. 6A illustrates the working arms 6 in a bipolar configuration 102 where the working arms 6 even in a bipolar position 22 are always askew and laterally offset a distance (O) so that as the working arms are moved towards and away from each other a tip portion 26 protrudes out the distance (O).

Figure 6B:
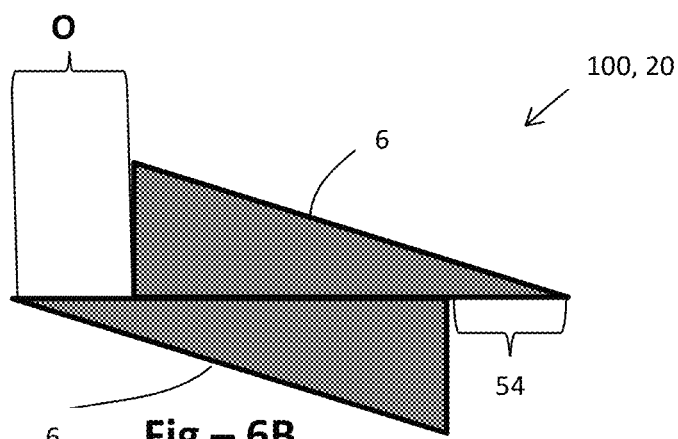
FIG. 6B illustrates a cross-sectional view of forceps tips askew and in contact.

FIG. 6B illustrates the working arms 6 in a monopolar configuration 100 where the working arms 6 are askew and laterally offset a distance (O). The working arms 6 in the monopolar position 20 maintain the same offset (O) as when the working arms are in the bipolar position 22 so that an edge electrode 54 extends beyond the opposing working arm 6.

Figure 7A:
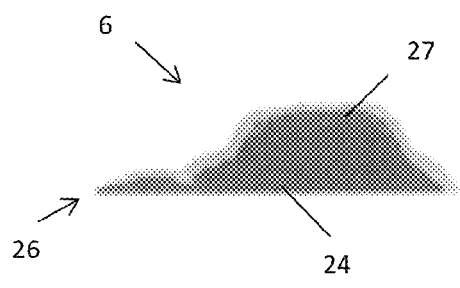
FIGS. 7A-7D illustrate alternative cross-sectional views of working arms for forceps.
Figure 7B:
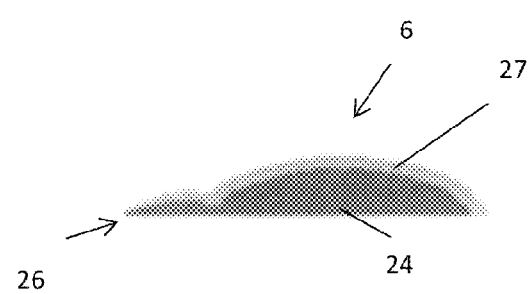
Figure 7C:
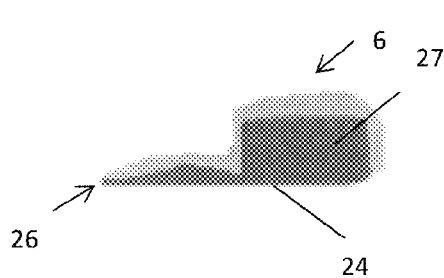
Figure 7D:
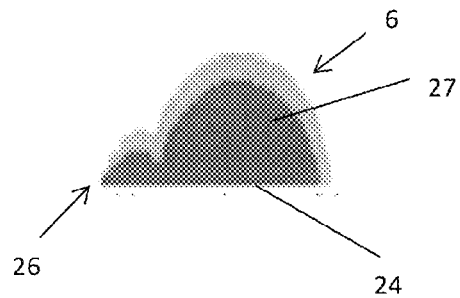

FIGS. 7A-7D illustrates various configurations of the working arms 6. The tip 26 of FIGS. 7A-7C have an electrode edge that extends to sharp pointed tip 26 and FIG. 7D has a blunt tip 26. The contact surface 24 of all four configurations are substantially flat so that when two working arms 6 towards each other the working surfaces 24 can be used as forceps (not shown). Each of the working arms 6 has a main body 27 connected to the tip 26. Each of the bodies 27 of FIG. 7A-7D have a different shape. For example, FIG. 7A has a rectangular shape with rounded corners, FIG. 7B has an arcuate low profile, FIG. 7C is rectangular, and FIG. 7D has a large bulbous portion.

Figure 8A:
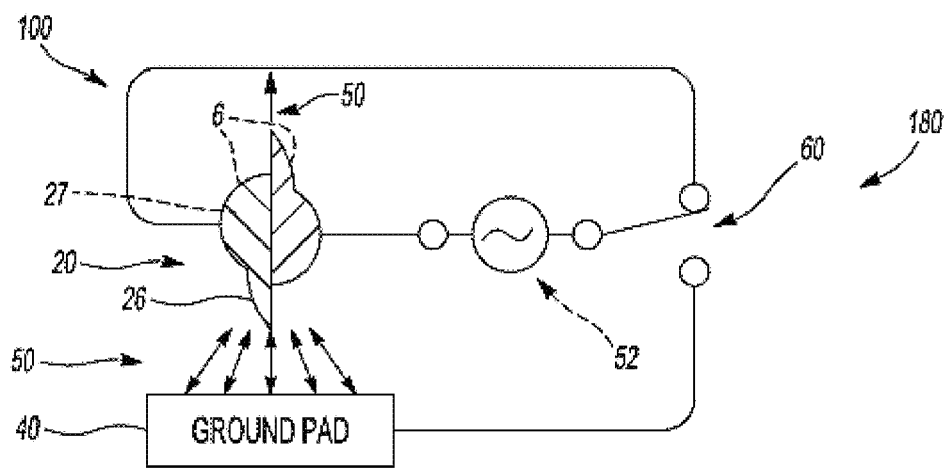
FIG. 8A illustrates an electrosurgical system including the forceps in a monopolar configuration.
Figure 8B:
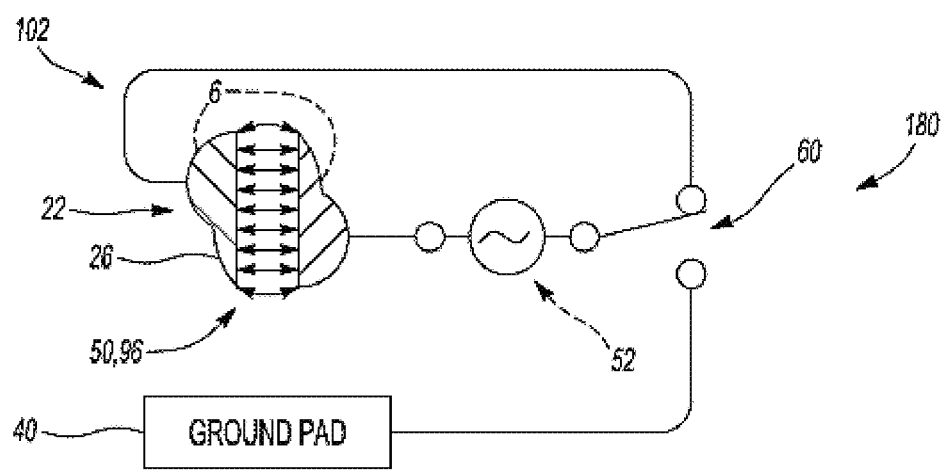
FIG. 8B illustrates an electrosurgical system including the forceps in a bipolar configuration.

FIGS. 8A and 8B illustrate the electrosurgical system 180 configured in the monopolar configuration 100 and the bipolar configuration 102 respectively. FIG. 8A illustrates the working arms 6 in a monopolar position 20 so that the working arms 6 are offset and the tips 26 extend beyond the body 27 of the opposing working arms 6. Power 50 flows from the tip 26 to a ground pad 40. When the working arms 6 are moved into the monopolar position 20 a switch 60 is moved electrically disconnecting one working arm 6 from being directly connected to the voltage source 52 and electrically connecting a ground pad 40 to the power source 52 so that a circuit is complete and power 50 flows between the ground pad 40 and the working arms 6.

FIG. 8B illustrates the working arms 6 in a bipolar position 22 so that the working arms 6 are separable relative to each other and the tips 26 of the working arms are aligned with the opposing working arm 6. Power 50 flows between the working arms 6 and any matter (not shown) in the contact region 96 between the working arms 6. When the working arms 6 are moved into the bipolar position 22 a switch 60 is moved electrically disconnecting a ground pad 40 from being directly connected to the voltage source 52 and electrically connecting a the disconnected working arm 6 to the power source so that a circuit is complete and power 50 flows between the working arms 6.

FIGS. 9A and 9B illustrate two possible configurations of the working arms 6 in the bipolar position 22. FIG. 9A illustrates an axis 30 in the body 27 of the working arms between the tip 26 and the connection region 28. The working arms 6 are configured so that the contact surfaces 24 are aligned. FIG. 9B illustrates an alternative configuration of the connection region 28 where the connection regions 28 include connection features 32 that lock when the working arms 6 are moved into a monopolar position (not shown).

FIG. 9C illustrates the working arms 6 of FIG. 5B gripping tissue 200 that extends through the contact region 96.

FIG. 10A-10C illustrate an example of a sequence of reconfiguring the working arms 6 of FIG. 9A from a bipolar position 22 (FIG. 10A) to a monopolar position 20 (FIG. 10C) so that the working arms 6 are rotationally offset. FIG. 10A has the working arms 6 in a bipolar position 22 with each working arm having an axis 30. FIG. 10B illustrates the working arms 6 rotating clockwise 34 (e.g., skewing direction 76) around the axis 30 so that the connection regions 28 are moved towards each other. FIG. 10C shows the working arms 6 in a finally rotated around the axis 30 and in the monopolar position 20 with the connection regions 28 in contact with each other and the arms being askew so that the contact surfaces 24 have a rotational offset relative to each other.

Figure 10D:
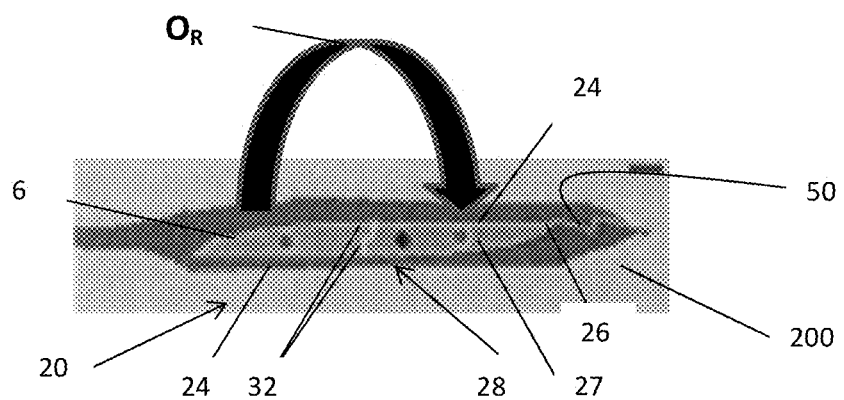
FIG. 10D illustrates the forceps in the monopolar position cutting tissue.

FIG. 10D illustrates the working arms 6 in the monopolar position 20 and power 50 flowing between a tip 26 and tissue 200. Each body 27 has connection features 32 in the connection region 28 that are locked together in a monopolar position 20 with the contact surfaces 24 being rotationally offset ($O_R$).

Figure 10E:
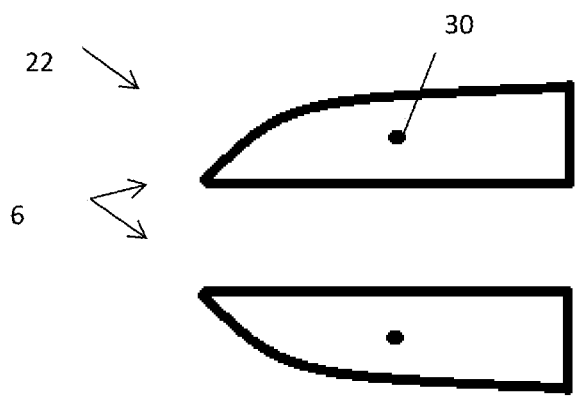
FIG. 10E illustrates an example of working arm in the bipolar position.
Figure 10F:
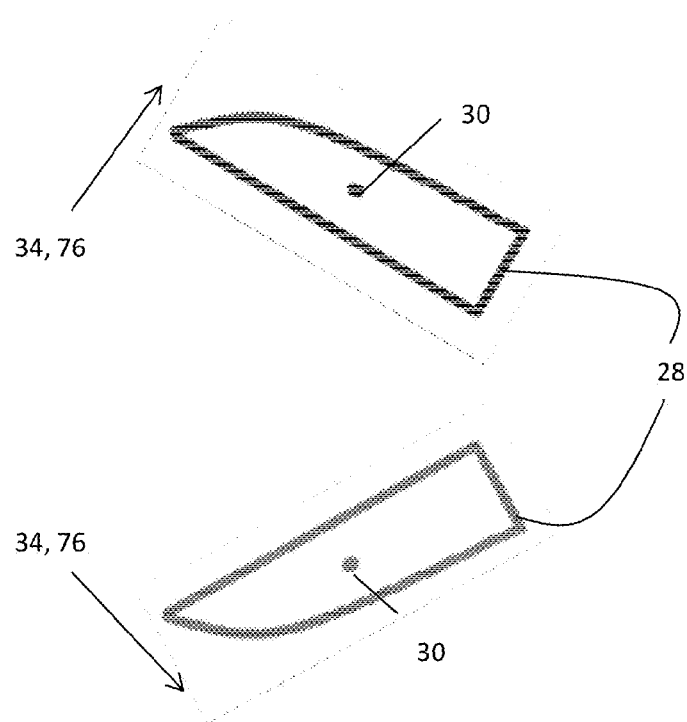
FIG. 10F illustrates an example of an alternative rotation of the forceps around axes.
Figure 10G:
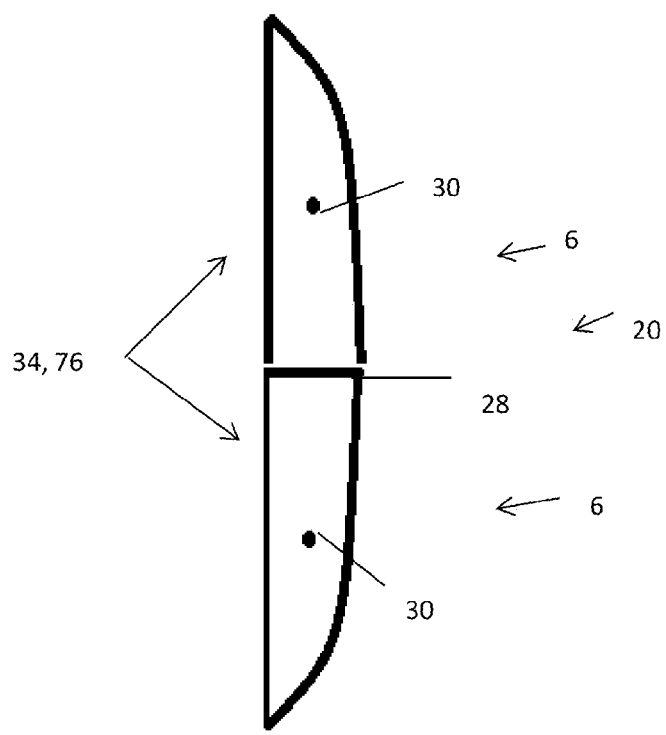
FIG. 10G illustrates the forceps in the monopolar position.

FIG. 10E-10G illustrate another example of a sequence of reconfiguring the working arms 6 from a bipolar position 22 (FIG. 10E) to a monopolar position 20 (FIG. 10G) so that the working arms 6 are rotationally offset. FIG. 10E has the working arms 6 in a bipolar position 22 with each working arm having an axis 30. FIG. 10F illustrates the working arms 6 rotating in opposing directions 34 (e.g., skewing direction 76) around the axis 30 so that the connection regions 28 are moved towards each other. FIG. 10G shows the working arms 6 in a position finally rotated around the axis 30 and in the monopolar position 20 with the connection regions 28 in contact with each other and the working arms 6 being askew so that the contact surfaces 24 have a rotational offset relative to each other but located on the same side of the working arms 6.

FIG. 11A illustrates an example of a pair of working arms 6 that in a bipolar position 22 are located substantially across from each other with the ends substantially aligned so that the working arms are not askew and there is substantially no offset (O'). The working arms 6 when in the bipolar position 22 move in a skewing direction 76 when used as forceps so that the working arms 6 are offset when in contact similar to when the working arms are in the monopolar position as is illustrated in FIG. 11B.

FIG. 11B illustrates the pair of working arms 6 when the working arms 6 are in the monopolar position 20 and the working arms 6 are askew. The working arms 6 are moved so that the working arms 6 have a lateral offset (O).

FIG. 12A illustrates two different sized working arms 6 so that one working arm is a smaller working arm 6A and one working arm is a bigger working arm 6B. The working arms 6 in the bipolar position 22 as illustrated move directly towards and away from each other when used as forceps. However, the tip 26 of the bigger working arm 6B always extends beyond the smaller working arm 6A so that the working arms 6 are in an askew configuration relative to each other.

FIG. 12B illustrates the smaller working arm 6A and bigger working arm 6B in the monopolar position 20 so that the tip 26 of the bigger working arm 6B extends beyond the smaller working arm 6A at all times creating the working arms to be askew relative to each other. The tip 26 of the bigger working arm 6B extends a lateral offset distance (O) beyond the smaller working arm 6A.

Figure 13A:
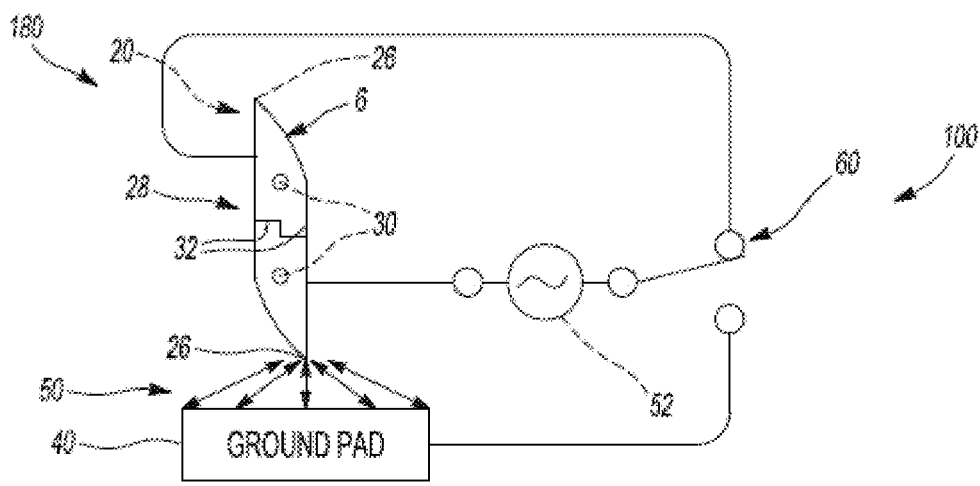
FIG. 13A illustrates the forceps of FIG. 10C in an electrosurgical system.
Figure 13B:
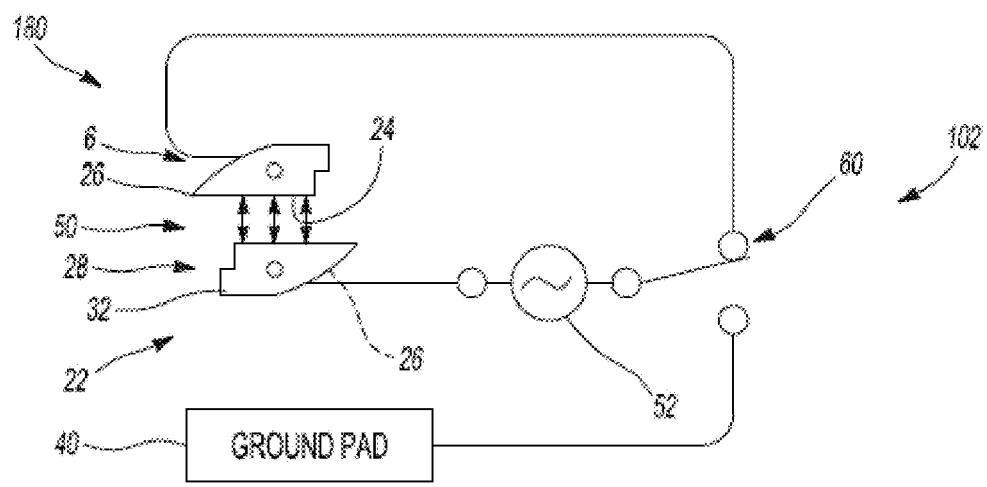
FIG. 13B illustrates the forceps of FIG. 9A or 10A in an electrosurgical system.

FIGS. 13A and 13B illustrate the electrosurgical system 180 configured in the monopolar configuration 100 and the bipolar configuration 102 respectively. FIG. 12A illustrates the working arms 6 in a monopolar position 20 so that the working arms 6 are each rotated about their axis 30 and the tips 26 are longitudinally aligned and the connection features 32 in the connection regions 28 are locked together. Power 50 flows from the tip 26 to a ground pad 40. When the working arms 6 are moved into the monopolar position 20 a switch 60 is moved electrically disconnecting one working arm 6 from being directly connected to the voltage source 52 and electrically connecting a ground pad 40 to the power source so that a circuit is complete and power 50 flows between the ground pad 40 and the working arms 6.

FIG. 13B illustrates the working arms 6 in a bipolar position 22 so that the working arms 6 are separable relative to each other and the tips 26 and contact surfaces 24 of the working arms 6 are opposite and aligned with the opposing working arm 6. The connection regions 28 each include a connection feature 32 that is unlocked in the bipolar position 22. Power 50 flows between the working arms 6 and any matter (not shown) between the working arms 6. When the working arms 6 are moved into the bipolar position 22 a switch 60 is moved electrically disconnecting a ground pad 40 from being directly connected to the voltage source 52 and electrically connecting a the disconnected working arm 6 to the power source so that a circuit is complete and power 50 flows between the working arms 6.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

I claim:

1. An electrosurgical device comprising:
   a forceps including:
   (i) a first working arm having a contact surface;
   (ii) a second working arm having a contact surface;
   (iii) a skewing device connected to both the first working arm and the second working arm, wherein the skewing device includes a pathway located on a side of the skewing device and proximate to the first working arm or the second working arm;
   (iv) a pin connected to the first working arm or the second working arm and located within the pathway;
   (vi) a bias feature connected to the skewing device so that application of a force on the bias feature moves the skewing device along the pin located within the pathway so that the forceps move between a first electrical configuration and a second electrical configuration,
   wherein when the forceps is in the first electrical configuration the contact surface of the first working arm and the contact surface of the second working arm are directly opposing, facing, and aligned with each other and are laterally movable relative to each other, and during lateral movement in the first electrical configuration the contact surface of the first working arm and the contact surface of the second working arm remain directly opposing, facing, and aligned with each other and the contact surface of the first working arm and the contact surface of the second working arm can be used to grip an item between the first working arm and the second working arm so that the forceps is configured to deliver a first therapy current through the first working arm, the second working arm, or both;
   wherein when the forceps is in the second electrical configuration the contact surface of the first working arm and the contact surface of the second working arm face each other, are in planar contact, and askew relative to each other and an electrode edge is formed on at least one side of the forceps so that a second therapy current extends from the electrode edge;
   wherein both the first working arm and the second working arm are configured to be electrically connected to a voltage source, in the first electrical configuration, so that the first therapy current flows between the first working arm and the second working arm; and wherein the first working arm is configured to be electrically disconnected from the voltage source, the second working arm is configured to be electrically connected to the voltage source, and a return electrode is configured to be electrically connected to the voltage source, in the second electrical configuration, so that the second therapy current flows between the return electrode and the second working arm which is connected to the voltage source.

2. The electrosurgical device of claim 1, wherein the first electrical configuration is a bipolar configuration and the second electrical configuration is a monopolar configuration.

3. The electrosurgical device of claim 2, wherein the first working arm has a first working arm electrode edge on a first side of the forceps and the second working arm has a second working arm electrode edge on a second side of the forceps; and the first working arm electrode edge and the second working arm electrode edge extend in opposite directions when the forceps are in the monopolar configuration, in the bipolar configuration, or both and the first working arm electrode edge, the second working arm electrode edge, or both are the electrode edge.

4. The electrosurgical device of claim 3, wherein the electrode edge is a tip and the tip is blunt so that the tip cannot mechanically cut tissue.

5. The electrosurgical device of claim 2, wherein the first working arm and the second working arm are aligned in the bipolar configuration, when the first working arm and the second working arm are separated, or both; and the first working arm and the second working arm are askew when the first working arm and the second working arm in the monopolar configuration, are in contact, or both.

6. The electrosurgical device of claim 2, wherein when the first working arm and the second working arm are askew in the monopolar configuration, the electrode edge is part of the first working arm and is offset and extends beyond a body of the second working arm.

7. The electrosurgical device of claim 2, wherein when the first working arm and the second working arm are askew in the monopolar configuration, the electrode edge includes a first electrode edge and a second electrode edge;

wherein the first electrode edge is part of the first working arm and is offset and extends beyond a body of the second working arm, and wherein the second electrode edge is part of the second working arm and is offset and extends beyond a body of the first working arm.

8. The electrosurgical device of claim 2, wherein when the contact surface of the first working arm and the contact surface of the second working arm when brought into contact form the electrode edge on the at least one side of the forceps so that the forceps is configured to cut tissue with the electrode edge.

9. The electrosurgical device of claim 1, wherein the second electrical configuration is a monopolar configuration.

10. The electrosurgical device of claim 1, wherein the contact surface of the first working arm and the contact surface of the second working arm when brought into contact form the electrode edge on the at least one side of the forceps so that the forceps is configured to cut tissue with the electrode edge.

11. The electrosurgical device of claim 10, wherein the electrode edge is a mechanical blade.

12. The electrosurgical device of claim 11, wherein the first working arm and the second working arm are askew in the second electrical configuration, or a position between the first electrical configuration and the second electrical configuration.

13. The electrosurgical device of claim 10, wherein the electrode edge is a tip on the first working arm and a tip on the second working arm and the first therapy current, the second therapy current, or both extends from the tip on the first working arm, the tip on the second working arm, or both individually or simultaneously.

14. The electrosurgical device of claim 10, wherein the electrode edge is a monopolar electrode.

15. The electrosurgical device of claim 11, wherein the electrode edge is a monopolar electrode.

16. The electrosurgical device of claim 1, wherein the first working arm and the second working arm are askew in the second electrical configuration or a position between the first electrical configuration and the second electrical configuration.

17. The electrosurgical device of claim 1, wherein the electrode edge is a tip on the first working arm and a tip on the second working arm and the first therapy current, the second therapy current, or both extend from the tip on the first working arm, the tip on the second working arm, or both individually or simultaneously.

18. The electrosurgical device of claim 1, wherein the electrode edge is a tip and the tip is blunt so that the tip cannot mechanically cut tissue.

19. A method comprising:
a. providing an electrosurgical device including:
   (i) a first working arm having a contact surface;
   (ii) a second working arm having a contact surface;
   (iii) a skewing device connected to both the first working arm and the second working arm, wherein the skewing device includes a pathway located on a side of the skewing device proximate to the first working arm or the second working arm;
   (iv) a pin connected to the first working arm or the second working arm and located within the pathway;
   (v) a bias feature connected to the skewing device so that application of a force on the bias feature moves the skewing device along the pin located within the pathway so that the first working arm and the second working arm move between a bipolar configuration and a monopolar configuration;
b. moving the first working arm and the second working arm towards each other by applying the force on the bias feature so that the first working arm and the second working arm are forceps and are configured in the bipolar configuration so that a first therapy current can pass between the first working arm and the second working arm and in the bipolar configuration, the contact surface of the first working arm and the contact surface of the second working arm are directly opposing and aligned with each other and are laterally movable relative to each other so that the contact surface of the first working arm and the contact surface of the second working arm can be used to grip an item between the first working arm and the second working arm; and
c. configuring the first working arm and the second working arm into the monopolar configuration by applying an opposing force on the bias feature so that the contact surface of the first working arm and the contact surface of the second working arm face each other, are in planar contact, and askew relative to each other and an electrode edge is formed on at least one side of the forceps and in the monopolar configuration a second therapy current can extend from the electrode edge.

20. The method of claim 19, wherein during the step of configuring the first working arm and the second working arm so that they are askew, the first working arm is moved in a first direction, the second working arm is moved in a second direction, or both so that a tip of the first working arm extends beyond a body of the second working arm and a tip of the second working arm extends beyond a body of the first working arm and the first and second working arms are offset relative to each other.

\* \* \* \* \*